(12) United States Patent
Hunziker et al.

(10) Patent No.: US 12,102,840 B2
(45) Date of Patent: *Oct. 1, 2024

(54) DERMATOLOGICAL LASER TREATMENT SYSTEMS AND METHODS USING OPTICAL PARAMETRIC OSCILLATOR

(71) Applicant: Cutera, Inc., Brisbane, CA (US)

(72) Inventors: Lukas E. Hunziker, San Jose, CA (US); Michael A. Karavitis, San Pedro, CA (US); Hsiao-Hua Liu, Brisbane, CA (US)

(73) Assignee: Cutera, Inc., Brisbane, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 17/868,732

(22) Filed: Jul. 19, 2022

(65) Prior Publication Data

US 2022/0362575 A1 Nov. 17, 2022

Related U.S. Application Data

(63) Continuation of application No. 16/882,405, filed on May 22, 2020, now Pat. No. 11,400,308, which is a continuation-in-part of application No. 15/820,421, filed on Nov. 21, 2017, now Pat. No. 10,729,496.

(60) Provisional application No. 62/851,615, filed on May 22, 2019.

(51) Int. Cl.
*A61N 5/06* (2006.01)
*A61N 5/067* (2006.01)

(52) U.S. Cl.
CPC .... *A61N 5/0616* (2013.01); *A61N 2005/0631* (2013.01); *A61N 2005/0651* (2013.01); *A61N 5/067* (2021.08)

(58) Field of Classification Search
CPC .......... A61B 2017/00157; A61B 2017/00768; A61B 2017/1807; A61B 2017/202; A61B 2017/00452
See application file for complete search history.

(56) References Cited

U.S. PATENT DOCUMENTS

| | | |
|---|---|---|
| 5,017,806 A | 10/1991 | Cheng et al. |
| 5,066,291 A | 11/1991 | Stewart |
| 5,117,126 A | 5/1992 | Geiger |
| 5,365,366 A | 11/1994 | Kafka et al. |

(Continued)

FOREIGN PATENT DOCUMENTS

| | | |
|---|---|---|
| WO | 1999049937 A1 | 10/1999 |
| WO | 2007127924 A2 | 11/2007 |

(Continued)

OTHER PUBLICATIONS

Anderson, Rox R. et al., "Selective Photothermolysis of Lipid-Rich Tissues: A Free Electron Laser Study," Lasers in Surgery & Medicine 38:913-919 (2006), Wiley Interscience.

(Continued)

*Primary Examiner* — Brian T Gedeon
(74) *Attorney, Agent, or Firm* — McCarter & English, LLP

(57) ABSTRACT

Dermatological systems and methods for providing picosecond laser pulses at a plurality of treatment wavelengths, wherein at least one of the wavelengths is provided by an optical parametric oscillator (OPO) capable of providing laser pulses at a wavelength for treating one or more target tissue types. In some embodiments, multiple OPOs may be provided to enable a wide range of selectable treatment wavelengths.

20 Claims, 13 Drawing Sheets

(56) References Cited

U.S. PATENT DOCUMENTS

| | | |
|---|---|---|
| 5,454,808 A | 10/1995 | Koop et al. |
| 5,520,679 A | 5/1996 | Lin |
| 5,556,372 A | 9/1996 | Talish et al. |
| 5,579,152 A | 11/1996 | Ellingson et al. |
| 5,594,592 A | 1/1997 | Harlamoff et al. |
| 5,619,517 A | 4/1997 | Dixon |
| 5,634,922 A | 6/1997 | Hirano et al. |
| 5,661,595 A | 8/1997 | Stamm et al. |
| 5,662,643 A | 9/1997 | Kung et al. |
| 5,687,186 A | 11/1997 | Stultz |
| 5,742,626 A | 4/1998 | Mead et al. |
| 5,752,949 A | 5/1998 | Tankovich et al. |
| 5,754,333 A | 5/1998 | Fulbert et al. |
| 5,782,822 A | 7/1998 | Telfair et al. |
| 5,841,798 A | 11/1998 | Chen et al. |
| 5,885,211 A | 3/1999 | Eppstein et al. |
| 5,896,220 A | 4/1999 | Stamm et al. |
| 5,976,123 A | 11/1999 | Baumgardner |
| 5,979,454 A | 11/1999 | Anvari et al. |
| 5,995,522 A | 11/1999 | Scherrer et al. |
| 5,999,547 A | 12/1999 | Schneider et al. |
| 6,015,404 A | 1/2000 | Altshuler et al. |
| 6,016,214 A | 1/2000 | Meyer et al. |
| 6,026,816 A | 2/2000 | McMillan et al. |
| 6,044,094 A | 3/2000 | Govorkov |
| 6,101,022 A | 8/2000 | Chen et al. |
| 6,142,939 A | 11/2000 | Eppstein et al. |
| 6,200,308 B1 | 3/2001 | Pope et al. |
| 6,215,800 B1 | 4/2001 | Komine |
| 6,235,016 B1 | 5/2001 | Stewart |
| 6,241,720 B1 | 6/2001 | Nighan, Jr. et al. |
| 6,295,160 B1 | 9/2001 | Zhang et al. |
| RE37,504 E | 1/2002 | Lin |
| 6,358,243 B1 | 3/2002 | Esterowitz et al. |
| 6,408,212 B1 | 6/2002 | Neev |
| 6,433,918 B1 | 8/2002 | Kasai et al. |
| 6,488,696 B1 | 12/2002 | Cho et al. |
| 6,508,813 B1 | 1/2003 | Altshuler |
| 6,514,244 B2 | 2/2003 | Pope et al. |
| 6,517,532 B1 | 2/2003 | Altshuler et al. |
| 6,605,080 B1 | 8/2003 | Altshuler et al. |
| 6,610,049 B2 | 8/2003 | Lai et al. |
| 6,632,219 B1 | 10/2003 | Baranov et al. |
| 6,638,272 B2 | 10/2003 | Cho et al. |
| 6,647,034 B1 | 11/2003 | Smith et al. |
| 6,663,620 B2 | 12/2003 | Altshuler et al. |
| 6,702,838 B1 | 3/2004 | Andersen et al. |
| 6,723,090 B2 | 4/2004 | Altshuler et al. |
| 6,743,222 B2 | 6/2004 | Durkin et al. |
| 6,770,069 B1 | 8/2004 | Hobart et al. |
| 6,835,202 B2 | 12/2004 | Harth et al. |
| 6,963,443 B2 | 11/2005 | Pfeiffer et al. |
| 6,976,985 B2 | 12/2005 | Altshuler et al. |
| 6,991,644 B2 | 1/2006 | Spooner et al. |
| 6,997,923 B2 | 2/2006 | Anderson et al. |
| 7,016,103 B2 | 3/2006 | Paschotta et al. |
| 7,018,396 B2 | 3/2006 | Sierra et al. |
| 7,044,959 B2 | 3/2006 | Anderson et al. |
| 7,041,094 B2 | 5/2006 | Connors et al. |
| 7,060,061 B2 | 6/2006 | Altshuler et al. |
| 7,184,614 B2 | 2/2007 | Slatkine |
| 7,198,634 B2 | 4/2007 | Harth et al. |
| 7,204,832 B2 | 4/2007 | Altshuler et al. |
| 7,208,007 B2 | 4/2007 | Nightingale et al. |
| 7,211,060 B1 | 5/2007 | Talish et al. |
| 7,250,047 B2 | 7/2007 | Anderson et al. |
| 7,291,140 B2 | 11/2007 | MacFarland et al. |
| 7,326,199 B2 | 2/2008 | MacFarland et al. |
| 7,331,953 B2 | 2/2008 | Manstein et al. |
| 7,351,252 B2 | 4/2008 | Altshuler et al. |
| 7,367,341 B2 | 5/2008 | Anderson et al. |
| 7,410,469 B1 | 8/2008 | Talish et al. |
| 7,422,599 B2 | 9/2008 | Perez |
| 7,447,245 B2 | 11/2008 | Caprara et al. |
| 7,465,307 B2 | 12/2008 | Connors et al. |
| 7,470,270 B2 | 12/2008 | Azar et al. |
| 7,524,328 B2 | 4/2009 | Connors et al. |
| 7,616,304 B2 | 11/2009 | Gankkhanov et al. |
| 7,618,414 B2 | 11/2009 | Connors et al. |
| 7,686,839 B2 | 3/2010 | Parker |
| 7,703,458 B2 | 4/2010 | Levernier et al. |
| 7,722,600 B2 | 5/2010 | Connors et al. |
| 7,731,953 B2 | 6/2010 | Leonard et al. |
| 7,763,016 B2 | 7/2010 | Altshuler et al. |
| 7,780,652 B2 | 8/2010 | MacFarland et al. |
| 7,814,915 B2 | 10/2010 | Davenport et al. |
| 7,878,206 B2 | 2/2011 | Connors et al. |
| 7,891,362 B2 | 2/2011 | Domankevitz et al. |
| 7,942,153 B2 | 5/2011 | Manstein et al. |
| 7,955,282 B2 | 6/2011 | Doo |
| 7,975,702 B2 | 7/2011 | Cho et al. |
| 7,998,181 B2 | 8/2011 | Nightingale et al. |
| 8,002,768 B1 | 8/2011 | Altshuler et al. |
| 8,094,368 B2 | 1/2012 | Ebrahim-Zadeh et al. |
| 8,113,209 B2 | 2/2012 | Masotti et al. |
| 8,172,835 B2 | 5/2012 | Leyh et al. |
| 8,182,473 B2 | 5/2012 | Altshuler et al. |
| 8,190,243 B2 | 5/2012 | Welches et al. |
| 8,211,097 B2 | 7/2012 | Leyh |
| 8,244,369 B2 | 8/2012 | Kreindel |
| 8,275,422 B2 | 9/2012 | Allison |
| 8,276,592 B2 | 10/2012 | Davenport et al. |
| 8,285,390 B2 | 10/2012 | Levinson et al. |
| 8,317,779 B2 | 11/2012 | Mirkov et al. |
| 8,317,780 B2 | 11/2012 | Davenport et al. |
| 8,322,348 B2 | 12/2012 | Mirkov et al. |
| 8,328,796 B2 | 12/2012 | Altshuler et al. |
| 8,353,899 B1 | 1/2013 | Wells et al. |
| 8,366,703 B2 | 2/2013 | Davenport et al. |
| 8,380,306 B2 | 2/2013 | Pickett |
| 8,439,901 B2 | 5/2013 | Davenport et al. |
| 8,454,591 B2 | 6/2013 | Leyh et al. |
| 8,460,280 B2 | 6/2013 | Davenport et al. |
| 8,474,463 B2 | 7/2013 | Levernier et al. |
| 8,498,043 B2 | 7/2013 | Esteban-Martin et al. |
| 8,523,927 B2 | 9/2013 | Levinson et al. |
| 8,562,599 B2 | 10/2013 | Leyh |
| 8,585,618 B2 | 11/2013 | Hunziker et al. |
| 8,656,931 B2 | 2/2014 | Davenport et al. |
| 8,657,811 B2 | 2/2014 | Arai et al. |
| 8,702,769 B2 | 4/2014 | Eckhouse et al. |
| 8,702,774 B2 | 4/2014 | Baker et al. |
| 8,728,064 B2 | 5/2014 | Schomacker et al. |
| 8,771,263 B2 | 7/2014 | Epshtein et al. |
| 8,778,003 B2 | 7/2014 | Eckhouse et al. |
| 8,834,547 B2 | 9/2014 | Anderson et al. |
| 8,840,608 B2 | 9/2014 | Anderson et al. |
| 8,867,122 B2 | 10/2014 | Barr et al. |
| 8,870,856 B2 | 10/2014 | Connors et al. |
| 8,876,809 B2 | 11/2014 | Eckhouse et al. |
| 8,876,811 B2 | 11/2014 | Lewinsky et al. |
| 8,882,753 B2 | 11/2014 | Mehta et al. |
| 8,891,160 B2 | 11/2014 | Vodopyanov |
| 8,902,939 B2 | 12/2014 | Kafka et al. |
| 8,915,906 B2 | 12/2014 | Davenport et al. |
| 8,915,948 B2 | 12/2014 | Altshuler et al. |
| 8,920,409 B2 | 12/2014 | Davenport et al. |
| 8,932,278 B2 | 1/2015 | Tankovich et al. |
| 8,936,593 B2 | 1/2015 | Epshtein et al. |
| 8,939,966 B2 | 1/2015 | Hahn |
| 9,078,681 B2 | 7/2015 | Koifman et al. |
| 9,078,683 B2 | 7/2015 | Sabati et al. |
| 9,084,587 B2 | 7/2015 | Eckhouse et al. |
| 9,132,031 B2 | 9/2015 | Levinson et al. |
| 9,149,332 B2 | 10/2015 | Koifman et al. |
| 9,271,793 B2 | 3/2016 | Eckhouse et al. |
| 9,308,120 B2 | 4/2016 | Anderson et al. |
| 9,358,068 B2 | 6/2016 | Schomacker et al. |
| 9,375,345 B2 | 6/2016 | Levinson et al. |
| 9,486,285 B2 | 11/2016 | Paithankar et al. |
| 9,539,439 B2 | 1/2017 | Jones et al. |
| 9,597,528 B2 | 3/2017 | Schomacker et al. |
| 9,685,753 B2 | 6/2017 | Hellstrom et al. |
| 9,913,688 B1 | 3/2018 | Karavitis |

(56) References Cited

U.S. PATENT DOCUMENTS

| | | |
|---|---|---|
| 9,949,877 B2 | 4/2018 | Rubinchik et al. |
| 10,014,652 B2 | 7/2018 | Kafka et al. |
| 10,156,771 B2 | 12/2018 | Woodward, IV et al. |
| 10,305,244 B2 | 5/2019 | Sierra et al. |
| 10,434,324 B2 | 10/2019 | Mikrov et al. |
| 10,492,862 B2 | 12/2019 | Domankevitz |
| 10,517,676 B2 | 12/2019 | Schuster |
| 10,561,464 B2 | 2/2020 | Koifman et al. |
| 10,561,570 B2 | 2/2020 | Eckhouse et al. |
| 10,729,496 B2 | 8/2020 | Hunziker et al. |
| 10,864,380 B1 | 12/2020 | Karavitis et al. |
| 2001/0007068 A1 | 7/2001 | Ota et al. |
| 2002/0013575 A1 | 1/2002 | Lai et al. |
| 2002/0035360 A1 | 3/2002 | Connors et al. |
| 2002/0091377 A1 | 7/2002 | Anderson et al. |
| 2002/0123745 A1 | 9/2002 | Svaasand et al. |
| 2002/0161357 A1 | 10/2002 | Anderson et al. |
| 2002/0173782 A1 | 11/2002 | Cense et al. |
| 2003/0032950 A1 | 2/2003 | Altshuler et al. |
| 2003/0199859 A1 | 10/2003 | Altshuler et al. |
| 2004/0034319 A1 | 2/2004 | Anderson |
| 2004/0034341 A1 | 2/2004 | Altshuler et al. |
| 2004/0073079 A1 | 4/2004 | Altshuler et al. |
| 2004/0093042 A1 | 5/2004 | Altshuler et al. |
| 2004/0167499 A1 | 8/2004 | Grove et al. |
| 2005/0049582 A1 | 3/2005 | DeBenedictis et al. |
| 2005/0087198 A1 | 4/2005 | Bruno-Raimondi et al. |
| 2005/0171581 A1 | 8/2005 | Connors et al. |
| 2005/0215988 A1 | 9/2005 | Altshuler et al. |
| 2005/0251118 A1 | 11/2005 | Anderson et al. |
| 2005/0279369 A1 | 12/2005 | Lin |
| 2006/0084952 A1 | 4/2006 | Pallikaris et al. |
| 2006/0122668 A1 | 6/2006 | Anderson et al. |
| 2006/0282132 A1 | 12/2006 | Arai et al. |
| 2007/0073308 A1 | 3/2007 | Anderson et al. |
| 2007/0213695 A1 | 9/2007 | Peri et al. |
| 2007/0255362 A1 | 11/2007 | Levinson et al. |
| 2008/0009842 A1 | 1/2008 | Manstein et al. |
| 2008/0058784 A1 | 3/2008 | Manstein et al. |
| 2008/0214988 A1 | 9/2008 | Altshuler et al. |
| 2008/0215040 A1 | 9/2008 | Paithankar et al. |
| 2008/0221560 A1 | 9/2008 | Arai et al. |
| 2008/0269849 A1 | 10/2008 | Lewis |
| 2008/0319430 A1 | 12/2008 | Zenzie et al. |
| 2009/0024193 A1 | 1/2009 | Altshuler et al. |
| 2009/0069871 A1 | 3/2009 | Mahadevan-Jansen et al. |
| 2009/0112192 A1 | 4/2009 | Barolet et al. |
| 2009/0275927 A1 | 11/2009 | Mahadevan-Jansen et al. |
| 2009/0304033 A1 | 12/2009 | Ogilvy et al. |
| 2010/0049178 A1 | 2/2010 | Deem et al. |
| 2010/0179521 A1 | 7/2010 | Ghaffari et al. |
| 2010/0249893 A1 | 9/2010 | Aller |
| 2011/0137230 A1 | 6/2011 | Altshuler et al. |
| 2011/0284728 A1 | 11/2011 | Burdge et al. |
| 2012/0022518 A1 | 1/2012 | Levinson |
| 2012/0116271 A1 | 5/2012 | Caruso et al. |
| 2013/0043392 A1 | 2/2013 | Mildren |
| 2013/0066309 A1 | 3/2013 | Levinson |
| 2013/0066403 A1 | 3/2013 | Giraud et al. |
| 2013/0079684 A1 | 6/2013 | Rosen et al. |
| 2013/0184693 A1 | 7/2013 | Neev |
| 2013/0245725 A1 | 9/2013 | Mahadevan-Jansen et al. |
| 2014/0005760 A1 | 1/2014 | Levinson et al. |
| 2014/0257443 A1 | 9/2014 | Baker et al. |
| 2014/0277219 A1 | 9/2014 | Nanda |
| 2014/0277302 A1 | 9/2014 | Weber et al. |
| 2014/0296751 A1 | 10/2014 | Greenberg |
| 2014/0316393 A1 | 10/2014 | Levinson |
| 2014/0343462 A1 | 11/2014 | Burnet |
| 2014/0379052 A1 | 12/2014 | Myeong et al. |
| 2015/0051671 A1 | 2/2015 | Browne et al. |
| 2015/0202454 A1 | 7/2015 | Burnett |
| 2015/0216816 A1 | 8/2015 | O'Neil et al. |
| 2015/0223975 A1 | 8/2015 | Anderson et al. |
| 2015/0265492 A1 | 9/2015 | Eckhouse et al. |
| 2015/0328077 A1 | 11/2015 | Levinson |
| 2016/0051401 A1 | 2/2016 | Yee et al. |
| 2016/0310756 A1 | 10/2016 | Boll et al. |
| 2017/0304645 A1 | 10/2017 | Schomacker et al. |
| 2018/0036029 A1 | 2/2018 | Anderson et al. |
| 2018/0071024 A1 | 3/2018 | Harris |
| 2018/0140866 A1 | 5/2018 | Daly et al. |
| 2018/0177550 A1 | 6/2018 | Anderson et al. |
| 2019/0000529 A1 | 1/2019 | Kothare et al. |
| 2019/0374791 A1 | 12/2019 | Tagilaferri et al. |
| 2020/0315706 A1 | 10/2020 | Hunziker et al. |

FOREIGN PATENT DOCUMENTS

| | | |
|---|---|---|
| WO | 2008039557 A1 | 4/2008 |
| WO | 2008143678 A1 | 11/2008 |
| WO | 2014149021 A2 | 9/2014 |
| WO | 2014151872 A2 | 9/2014 |

OTHER PUBLICATIONS

Bashkatov, A. N., "Optical Properties of Human Skin, Subcutaneous and Mucous Tissues in the Wavelength Range From 400 to 2000 nm," J. Phys D: Appl. Phys., vol. 38, 2543-2555 (2005), Institute of Physics Publishing, UK.

Dewhirst, M.W. et al., "Basic Principles of Thermal Dosimetry and Thermal Thresholds for Tissue Damage from Hyperthermia," Int. J. Hyperthermia, vol. 19 No. 3, May-Jun. 2003, 267-294, T&F Online, UK.

Jacques, Steven L., and Daniel J. McAuliffe, "The Melanosome: Threshold Temperature for Explosive Vaporization and Internal Absorption Coefficient During Pulsed Laser Irradiation," Photochemistry and Photobiology, vol. 53, No. 6, 769-775 (1991), Pergamon Press plc, UK.

Karsten, Aletta, et al., "Modeling and Verication of Melanin Concentration on Human Skin Type," Photochemistry and Photobiology, vol. 88, 469-474 (2012), The American Society of Photobiology, US.

Keller, M. D. et al., "In Vitro Testing of Dual-Mode Thulium Microsurgical Laser," Photonic Therapeutics and Diagnostics VIII, ed. N. Kollias et al., Proc. of SPIE, vol. 8207, 820711-1 through 820711-8, 2012.

Li, X. C. et al., "Optical Properties of Edible Oils Within Spectral Range From 300 to 2500 nm Determined by Double Optical Pathlength Transmission Method," Applied Optics, vol. 54, No. 13, May 1, 2015, Optical Society of America, US.

Lloyd, Jenifer R., and Mirko Mirkov, "Selective Photothermolysis of the Sebaceious Glands for Acne Treatment," Lasers in Surgery and Medicine, vol. 31, 115-120 (2002), Wiley-Liss, Inc.

Paithankar, Dilip Y. et al., "Acne Treatment With a 1,450 nm Wavelength Laser and Cryogen Spray Cooling," Lasers in Surgery and Medicine, vol. 31, 106-114 (2002), Wiley-Liss, Inc.

Paithankar, Dilip Y. et al., "Subsurface Skin Renewal by Treatment With a 1450-nm Laser in Combination With Dynamic Cooling," Journal of Biomedical Optics, vol. 8, No. 3, 545-551, Jul. 2003 Lasers in Surgery and Medicine, vol. 31, 106-114 (Jul. 2003), SPIE.

Pearce, John A., "Relationship Between Arrhenius Models of Thermal Damage and the CEM 43 Thermal Dose," in Energy-Based Treatment of Tissue and Assessment V, ed. Thomas P. Ryan, Proc of SPIE vol. 7181, 718104-1 through 718104-15 (2009), SPIE.

Sakamoto, Fernanda H. et al., "Selective Photothermolysis to Target Sebaceous Glands: Theoretical Estimation of Parameters and Preliminary Results Using a Free Electron Laser," Lasers in Surgery and Medicine, vol. 44, 175-183 (2012), Wiley Periodicals, Inc.

Salomatina, Elena et al., "Optical Properties of Normal and Cancerous Human Skin in the Visible and Near-Infrared Spectral Range," J. Biomed. Optics., 11(6), Nov./Dec. 2006, 064026-1 through 064026-9, SPIE.

Tanghetti, Emil, Oral presentation, "A Histological Evaluation of Sebaceous Gland Damage With a 1726 nm Laser," Abstract Session, Clinical Applications—Cutaneous, Mar. 29, 2019, ASLMS 2019, Americal Society for Laser Medicine & Surgery, Inc.

(56) References Cited

OTHER PUBLICATIONS

Tanghetti, Emil, Oral presentation, "Laser Destruction of Sebaceous Glands: Threading the Needle," Special Sessions (CME), Cutting Edge: Laser and Skin, Mar. 30, 2019, ASLMS 2019, Americal Society for Laser Medicine & Surgery, Inc.
Ueno, Koichiro et al., "InSb Mid-Infrared Photon Detector for Room-Temperature Operation," Jpn. J. App. Phys., vol. 52, 092202-1 through 092202-6 (2013), The Japan Society of Applied Physics, Japan.
Vogel, Alfred et al., "Minimization of Thermomechanical Side Effects and Increase of Ablation Efficiency in IR Ablation by Use of Multiply Q-Switched Laser Pulses," Proc. SPIE vol. 4617A, Laser Tissue Interaction XIII,2002.
Wang, Lihong et al., "Monte Carol Modeling of Light Transport in Multi-layered Tissues in Standard C," University of Texas M.D. Anderson Cancer Center, XX-YY (1992), Dept. of the Navy, US.
Arisholm, Gunnar et al., "Limits to the Power Scalability of High-Gain Optical Parametric Amplifiers", J. Opts. Soc. Am B/vol. 21, No. 3, Mar. 2004, pp. 578-590, US.
Farsun, Oystein et al, "High-Pulse-Energy, Linear Optical Parametric Oscillator with Narrow and Symmetrical Far Field", Optical Society of America, vol. 21, No. 17, Aug. 26, 2013, Optics Express pp. 20171-20178, US.
Rustad, Gunnar et al., "Design of a High Pulse Energy Coherent Ultraviolet Source—Simulations and Experimental Design", Norwegian Defence Research Establishment (FFAI), Feb. 1, 2013, 61 pages, Norway.
Rustad, Gunnar et al., "Effect of Idler Absorption in Pulsed Optical Parametric Oscillators" Optical Society of America, vol. 19, No. 3, Jan. 31, 2011, Optics Express, pp. 2815-2830, US.
Smith, Arlee V. et al., "Nanosecond Optical Parametric Oscillator with 90 Image Rotation: Design and Performance," Journal of Optical Society of America, vol. 19, No. 8, Aug. 2002, pp. 1801-1814, US.
Notice of Allowance dated Aug. 13, 2020, U.S. Appl. No. 16/805,761, filed Feb. 29, 2020.
Office Action dated May 15, 2020, U.S. Appl. No. 16/805,761, filed Feb. 29, 2020.
Wenzel, H. et al., "Design and Realization of High-Power DFB Lasers", Proceedings of SPIE, vol. 5594, Bellingham, WA, pp. 110-123, 2004.
Ricci, L. et al., "A Compact Grating-Stabilized Diode Laser System for Atomic Physics" Optics Communications, 117 pp. 541-549, 1995.
Thompson, Daniel J. , et al., "Narrow Linewidth Tunable External Cavity Diode Laser Using Wide Bandwith Filter", Rev. Sci. Instrum. 83, 023107 (2012).
Vaissie, Laurent et al., "Bright Laser Diodes Combat Cancer", Bio Optics World, Jul./Aug. 2009.
Valle-Lopera, Diego Andres et al., "Test and Fabrication of Piezoresistive Sensors for Contact Pressure Measurement" Revista Facultad de Ingenieria, Medellin, Colombia, 82, pp. 47-52, 2017.
Suprapto, S.S. et al., "Low-Cost Pressure Sensor Matrix Using Velostat" 2017 5th ICICI-BME, Bandung, Nov. 6-7, 2017.
Interlink Electronics, "FSR 400 Series Datea Sheet".
Interlink Electronics, "Enhancing Medical Devices and Personal Healthcare Products with Force Sensing Technology", Feb. 2014.
Tekscan, "Best Practices in Electrical Integration of the FlexiForce Sensor".
Saccomandi, Paola et al., "Techniques for Temperature Monitoring During Laser-Induced Thermotherapy: An Overview," International Journal of Hyperthermia, vol. 29, No. 7, Sep. 13, 2019, 609-619, Informa UK Ltd, UK.
Nelson, J. Stuart et al., "Dynamic Epidermal Cooling During Pulsed Laser Treatment of Port-Wine Stain," Archives of Dermatology, vol. 131, Jun. 1995, 695-700, Americal Medical Association, US.
Tekscan, "Best Practices in Mechanical Integration of the FlexiForce Sensor".
Notice of Allowance dated Apr. 3, 2020, U.S. Appl. No. 15/820,421, filed Nov. 21, 2017.
Office Action dated Oct. 29, 2019, U.S. Appl. No. 15/820,421, filed Nov. 21, 2017.

DERMATOLOGICAL LASER TREATMENT SYSTEMS AND METHODS USING OPTICAL PARAMETRIC OSCILLATOR

CROSS REFERENCE TO RELATED APPLICATIONS

This application is a continuation of U.S. patent application Ser. No. 16/882,405, filed May 22, 2020, entitled "Dermatological Picosecond Laser Treatment Systems and Methods Using Optical Parametric Oscillator," which is a continuation-in-part of and claims the benefit of priority to U.S. patent application Ser. No. 15/820,421, filed Nov. 21, 2017, now U.S. Pat. No. 10,729,496, entitled "Dermatological Picosecond Laser Treatment Systems and Methods Using Optical Parametric Oscillator". U.S. patent application Ser. No. 16/882,405 also claims the benefit of priority to U.S. Provisional Application Ser. No. 62/851,615, filed May 22, 2019, and entitled "Dermatological Picosecond Laser Treatment Systems and Methods Using Optical Parametric Oscillator". The present application claims the benefit of priority to each of the foregoing applications, which are hereby incorporated by reference herein in their entirety.

BACKGROUND OF THE INVENTION

This invention relates generally to the field of electromagnetic-based medical treatment systems, and more specifically to systems and methods for treatment of dermatological conditions with lasers having at least one wavelength determined by an optical parametric oscillator.

A variety of dermatological conditions are treatable using electromagnetic radiation (EMR). Sources of EMR for such treatments include lasers, flashlamps, and RF sources, each of which has distinct advantage and disadvantage profiles. EMR devices have been used, for example, treating abnormal pigmentation conditions, body sculpting (e.g., removal of subcutaneous adipose tissue), hair removal, treatment of vascular skin conditions (e.g., spider veins), reduction of wrinkles and fine lines, and dyschromia, among other conditions. Abnormal pigmentation conditions may include tattoos and benign pigmented lesions associated with high local concentrations of melanin in the skin, such as freckles, age spots, birthmarks, lentigines, and nevi, among other pigmentation conditions. Both pulsed and continuous-wave (CW) laser systems have been used to treat pigmentation conditions, although pulsed lasers are more frequently used.

Most applications of EMR in medical fields use a laser to photo-thermally damage a target tissue while preserving surrounding or adjacent tissues or structures, thereby inducing a healing response in the damaged tissue. The principle of selective photothermolysis, first established in the early 1980s by Anderson and Parrish, was an important discovery that led to the development of a variety of laser applications as standard of care in many medical fields such as ophthalmology and dermatology. Selective photothermolysis involves thermally damaging a target tissue to promote a healing response. Ideally, the damage is highly localized to only the particular target tissue (e.g., a particular skin layer, or particular structures such as chromophores within a skin layer), with surrounding non-targeted tissues/structures remaining unaffected and thus available to facilitate the healing response in the targeted tissue.

As articulated by Anderson and Parrish, photothermolysis can be achieved when three conditions are met: 1) the wavelength of the laser is chose to have maximum absorption in the target tissue and minimal absorption in non-targeted or surrounding tissue; 2) the pulse duration of the laser should be equal to or less than (=<) the thermal relation time (TRT) of the target tissue; and 3) the laser fluence (i.e., energy per unit area) must be sufficient to exceed the thermal damage threshold of the target tissue. Together, these principles permit laser systems to be developed that deliver energy at specific wavelengths, pulse durations, and fluences that are precisely controlled energy to damage target tissue while leaving non-targeted surrounding tissues and structures unaffected.

Another key to medical laser system development has been the concurrent advancement of laser technology. Since the first demonstration of a 694 nm ruby laser nearly sixty years ago, lasers having been developed using a variety of materials to provide a range of laser emission wavelengths. Consistent with the principles of photothermolysis, a laser wavelength may be selected to target specific tissues and body structures that selectively absorb that wavelength, while leaving nearby tissues having minimal absorption of the selective wavelength unaffected or minimally affected.

Examples include carbon dioxide lasers, developed in 1963 with a wavelength of 10,600 nm, neodymium YAG lasers, developed in 1964 with wavelengths of 532 and 1064 nm, organic dye lasers, developed in 1966 with a variety of wavelengths (for example, 585 and 595 nm), and alexandrite lasers, developed in 1979 and having a wavelength of 755 nm. Since the wavelength range of absorption varies with tissue type, having a wide selection of laser wavelengths is critical to meeting the first requirement of selective photothermolysis (maximum absorption in the target tissue) for multiple tissues and thereby enabling a variety of applications. Following these inventions, multiple products subsequently emerged having many different laser sources and wavelengths tailored to target a specific tissue and application. For example, pulsed dye laser (PDL) systems were developed for vascular applications since their emission wavelength overlaps well with the absorption band of hemoglobin. Carbon dioxide lasers were employed for skin resurfacing since their 10,600 nm emission is strongly absorbed by water, the primary chromophore in the dermis.

While individual laser systems tailored for specific applications (e.g., treatment of specific tissues in specific medical applications) works well, it requires a clinic or physician to purchase multiple systems to cover a full range of applications in a particular medical practice. This has led to the development of products with multiple lasers (e.g., having different capabilities of wavelength/frequency, pulse width/duration, pulse energy and peak energy), which provides some benefit but results in systems having higher cost, greater size/bulk, and complexity because of the higher number of system components.

More significantly, the number of laser wavelengths available from practical, proven laser media, though significant at present, still fails to cover the primary absorption bands for a number of important tissue types. For example, commercially viable laser sources having emission wavelengths in the near infrared (e.g., 780-2500 nm) and mid infrared (e.g., >2500 nm up to 10,000 nm) at clinically relevant output levels (e.g., pulse width & pulse energy) are especially limited. For example, the absorption bands of sebum (relevant for treating acne) include absorption peaks at 1727 nm and 2305 nm. Similarly, the absorption band for collagen includes peaks at 6049 nm and 6476 nm. The lack of available laser sources at these emission wavelengths has imposed significant limitations on the development of flexible systems capable of treating these tissues. Similar limitations exist for other tissue types.

There is a need for systems having a wavelength tunable laser source that is capable of providing laser emissions at wavelengths suitable for treating a variety of tissue types. A variety of laser materials exist that are capable of producing laser emission over a broad, continuous spectral (wavelength/frequency) range, and are therefore tunable in the strict sense. These include organic dyes, semiconductors, and some inorganic crystalline materials. However, significant technical barriers to such wavelength tunable laser sources have hindered development efforts.

One significant barrier to viable wavelength-tunable systems lies in the fact that the strength of the laser emission cross-section is inversely proportional to the tunable range. Consequently, broadband tunable laser materials generally have low output powers that are unsuitable to applications requiring high pulse energies. Applications in dermatology, for example, typically require treatment of relatively large body areas (e.g., 1 to 100 cm2), requiring high pulse energies on the order of 100 mJ to 100 J per pulse to maintain therapeutic fluences over the area to be treated. For this reason, broadband laser materials are not suitable for many medical applications. In addition to the poor output power, the tunable range of such materials is typically too narrow to selectively target more than one tissue type. Dermatological tissues may require output wavelengths ranging from, e.g., visible wavelengths of approximately 500 nm to infrared wavelengths exceeding 10,000 nm. Currently available laser materials are inadequate to achieve such a wide range of emission wavelengths with sufficient output powers to treat a full range of medical conditions, and there is a need for systems capable of providing a variety of different wavelengths for treating a variety of tissue types.

In addition to the capability of producing a wide range of laser wavelengths, dermatological laser systems capable of very short pulse durations are also needed to treat a wide range of conditions. As noted, successful photothermolysis requires that the pulse duration pulse of the laser should be less than or equal to the thermal relation time (TRT). Heating in tissues depends upon both the absorption coefficient of the irradiated tissue structures for the wavelength of laser light used, as well as their thermal relaxation times (TRT), which is a measure of how rapidly the affected structure returns to its original temperature. Nanosecond lasers have been used for decades to treat pigmented lesions and tattoo removal. Nanosecond lasers, as used herein, are pulsed lasers having a pulse duration or pulse width (PW) of greater than 1 nanosecond (nsec) up to 1 microsecond (µsec). By delivering the laser energy in a pulse with a very short time duration, highly localized heating (and destruction) of a tissue target structure (e.g., melanin, ink particles, collagen) can be achieved, thereby minimizing damage to non-target structures (e.g., non-targeted skin layers, blood vessels, etc.). If the laser pulse duration is less than the TRT of the target tissue, no significant heat can escape into non-target structures, and damage to non-target structures is limited.

More recently, the availability of picosecond laser pulses has ushered in a new paradigm in tattoo removal because they offer the ability to target tattoo ink particles at pulse widths that are equal or less than the TRT of the ink particles. As used herein, picosecond lasers are pulsed lasers having a pulse width or duration of 1 picosecond (psec) up to (and preferably below) 1 nsec. Studies have shown that the diameter of tattoo ink particles can range from 35 nm to 200 nm, with clusters as large as 10 µm. To clear the tattoo ink, the particles must be broken up into smaller fragments that can be cleared by the body. To break the particles up effectively, the laser energy must be delivered within the TRT of the particle, since the energy that escapes into the surrounding tissue not only damages non-target structures but also is unavailable to break down the target structure. A simple dimensional analysis shows that the TRT of a spherical particle scales with the square of its diameter, and ink particles smaller than about 150 nm will have relaxation times below 1 ns.

While the pulse duration for nanosecond lasers is generally less than the TRT for melanin in the skin, the small size of many ink particles in tattoos can result in TRT times of less than 1 nanosecond for those particles. Conventional Q-switched nanosecond lasers, which produce pulses of 5-20 nsec in duration, may result in ineffective ink removal as well as damage to tissue structures as the pulsed laser energy escapes into adjacent non-target tissue structures after the lapse of the TRT of the ink particles. This is particularly true for lasers having wavelengths that are highly absorbed by the non-target structures. Studies have shown that the use of picosecond lasers instead of nanosecond lasers can reduce the number of treatment sessions required to clear tattoos by a factor of 3.

Picosecond laser pulses may offer less tissue damage and higher safety margins for pigmented lesions, in addition to their superior performance for tattoo removal. The potential for improved clinical outcomes using picosecond lasers has resulted in commercially available systems having pulse widths of 500-1000 psec with pulse energies (i.e., energy per pulse) exceeding 100 mJ. On the other hand, high-energy picosecond lasers are much more complex and costly than any other energy-based treatment systems in the dermatology market today, and there is a need for more flexible, less expensive picosecond laser systems having a wide range of available wavelengths to treat a wide range of conditions. Additional details on treatment on treatment of tattoos is provided in related U.S. patent application Ser. No. 15/820, 421.

The first commercial dermatological picosecond laser systems used either a single 755 nm lasing wavelength, with alexandrite as the lasing medium, or dual 1064 nm and 532 nm laser wavelengths using Nd:YAG lasers. The 755 nm and 1064 nm wavelengths are part of the near-infrared portion of the electromagnetic spectrum, and are well-suited to removal of black tattoo inks due to their broad absorption spectra. The 532 nm wavelength is in the green portion of the visible spectrum, and is well-suited to removal of red inks which strongly absorb green light (the complementary color of red).

Because black and red are the most common tattoo colors, dual wavelength (532 nm and either 755 or 1064 nm) picosecond systems are the most common systems available. However, green and blue inks occur in about one-third of tattoos, and the absorption strength for these inks is greatest in the red portion of the visible spectrum. Accordingly, there is a need for a red wavelength in addition to the dual wavelength 1064/755, 532 nm (near infrared and green) picosecond laser systems to facilitate removal of green and blue inks. In view of the already-high cost of picosecond laser systems, the addition of a red wavelength must be done at a low cost, and in a flexible system that allows different wavelengths of light to be selected quickly and easily.

Because of their versatility, dual wavelength (1064/755, 532) picosecond systems are widely used to treat benign pigmented lesions, which involve the removal of melanin particles from the skin. Pulsed light at 532 nm is highly absorbed by melanin, while 1064 nm light absorbed less than 10% as well (absorption coefficients of 55.5 mm$^{-1}$ and 4.9 mm$^{-1}$) poorly absorbed. In addition, penetration depth of laser light falls rapidly with wavelength. Therefore, 532 nm laser light is effective at aggressive treatment of shallow pigment and 1064 nm light is more commonly used for milder but deeper treatment. It would be useful to have a third wavelength with an intermediate absorption in melanin, which could also help minimize potential damage to blood vessels in the superficial dermis, and maximize the absorption of melanin relative to hemoglobin.

Pulsed red light has been provided in prior art laser systems by laser-induced florescence of organic dyes. However, dye-based laser systems have a number of drawbacks. Typically, excitation is provided by a 532 nm (green light) Nd:YAG pulsed laser, with the red emission wavelength determined by the specific dye being used. Wavelengths of 585, 595, and 650 nm have been provided. The minimum pulse duration is defined by the fluorescence lifetime of the dye, which is typically between 1-5 ns, precluding their use in picosecond laser systems. Incoherent (non-laser) light may be captured optically and focused onto a treatment plane.

In some systems, the dye cells may be used as the gain medium in a laser cavity to produce laser emission, in which case picosecond pulses are possible because the pulse duration is approximately equal to that of the excitation laser. However, the cost of assembling such systems is significantly increased relative to systems that do not require dyes, and becomes prohibitive if the dye cells must be replaced frequently.

A more fundamental limitation of dye systems is their susceptibility to optical degradation. Both output energy and beam profile uniformity fall rapidly with operation, typically within 10,000 laser shots or pulses. Fluence of the beam at the treatment plane therefore becomes irregular and continues to change over time, leading to poor clinical outcomes. Emission also tends to have low spatial coherence, making it difficult to deliver the beam through a fiber or articulated are to an applicator, such as a handpiece, for application to the patient.

Because of optical degradation issues, dye cells are typically designed as a consumable item that attaches to the end of the applicator (e.g., a handpiece). While this allows the user to change the dye cell when performance drops, restoring beam uniformity and fluence, it introduces several limitations. First, in multi-wavelength systems the dye cell must be removed to change wavelengths, which is inconvenient to the user and patient during removal of multi-colored tattoos requiring multiple wavelengths in a single treatment session. Second, because the dye cell is near the point of application, integration of photometry to detect the optical degradation is difficult because of space limitations. In spite of these limitations, dye cells have seen limited but consistent use in the field for decades because of their ability to provide multiple laser wavelengths.

Another known method for generating red-wavelength picosecond laser pulses is through second harmonic generation, in which the frequency of the pumping laser is doubled, resulting in an output having wavelengths that are half that of the pumping laser. For example, Nd:YAG lasing wavelengths such as 1319 or 1338 nm may be frequency doubled with nonlinear crystals to produce red picosecond pulses at 659 and 669 nm. However, pumping wavelengths capable of frequency doubling to provide red laser light have relatively low optical gain, making the cost and complexity at these wavelengths significantly greater than existing 1064 and 532 nm dual wavelength systems. In addition, wavelengths in the 1300 nm range have limited use for dermatology, and such systems would have only one wavelength of significant value unless more than one laser engine is provided in the system, which would significantly increase system complexity, cost and bulk. Such systems are not economical and have not been commercialized.

Finally, laser architectures outside of the red spectral region have been developed, but these systems sacrifice clinical efficacy because of the non-optimal wavelengths. For example, picosecond laser systems are available that produce 755 nm, near-infrared pulses using alexandrite as the lasing medium, as well as systems that using 532 nm picosecond pulses to pump a titanium sapphire oscillator.

In addition to picosecond systems with visible light wavelengths to treat pigmented lesion, there is a need for systems capable of producing wavelengths in the near, medium, and far infrared systems for treatment of other tissues. More specifically, there is a need for picosecond pulse laser systems capable of treating conditions in the near-infrared range (approximately 780-2500 nm wavelengths) and in the mid-infrared range (approximately 2500-10,000 nm wavelengths). These include, for example, treatment of acne by targeting sebum, which has absorption peaks at 1726 and 2305 nm in the near-infrared range, and a number of conditions involving collagen (e.g., wrinkles), which has absorption peaks at 6049 nm and 6476 nm in the mid-infrared range. The lack of tunable laser sources at these emission wavelengths with sufficient pulse power has imposed significant limitations on the development of flexible systems capable of treating such.

There is a need for dermatological picosecond laser systems that are able to efficiently treat a variety of medical conditions using picosecond pulse widths and a wide range of wavelengths from the visible to the mid-infrared, and which are relatively compact, non-bulky and easy to use. There is also a need for dermatological picosecond laser systems having a simplified construction with fewer components, which are capable of providing a variety of laser wavelengths for treatment of a wide variety of pigmentation conditions and skin conditions, and allow a user to switch from a first to a second treatment wavelength quickly and easily.

SUMMARY

In one embodiment, the invention comprises a dermatological treatment system for treating a plurality of skin conditions using pulsed laser light having a selected wavelength, comprising: a laser engine adapted to output pulsed laser light having a first wavelength of from 500-1200 nm, a pulse width of 10 psec to 10 nsec, and a first pulse energy of from 100 mJ/pulse to 5 J/pulse; and at least one optical parametric oscillator (OPO) adapted to receive pulsed laser light from the laser engine and to generate OPO output pulses having a second wavelength selected from a wavelength at which sebum tissue has a higher absorption coefficient than water and a wavelength at which collagen tissue has a higher absorption coefficient than water, wherein the OPO output pulses comprise one of OPO signal pulses and OPO idler pulses; and an applicator adapted to receive and apply a selected one of the pulsed laser light output from the laser engine and the OPO output pulses to a target body tissue comprising sebum tissue, collagen tissue, and a third tissue that is neither sebum nor collagen.

In one embodiment, the invention comprises an optical parametric oscillator (OPO) system for use in a dermatological laser treatment system, the OPO system comprising: an input coupler for receiving laser input pulses having a pulse width of from 10 psec to 100 nsec and a first wavelength, the input coupler comprising a mirror having a high transmission (HT) at the first wavelength and a high reflectance (HR) at one of an OPO signal wavelength and an OPO idler wavelength; a resonant cavity including a non-linear crystal having a crystal length between 5 and 40 mm, wherein the resonant cavity produces OPO output pulses in response to receiving the laser input pulses, the OPO output pulses having a second wavelength selected from a wavelength at which sebum tissue has a higher absorption coefficient than water and a wavelength at which collagen tissue has a higher absorption coefficient than water, wherein the OPO output pulses comprise one of OPO signal pulses and OPO idler pulses; and an output coupler comprising a mirror having a high reflectance (HR) at the first wavelength and transmitting a selected portion of the second wavelength.

DESCRIPTION

Figure 1:
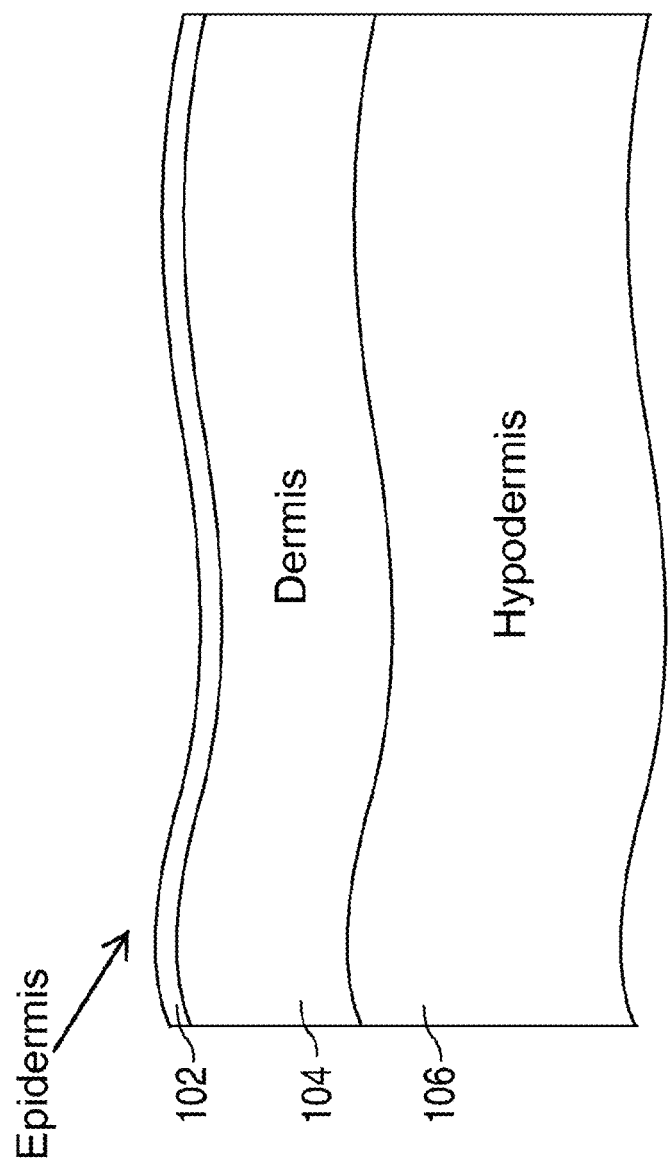
FIG. 1 is a cross-sectional illustration of skin tissue.

Exemplary embodiments of the present disclosure are illustrated in the drawings, which are illustrative rather than restrictive. No limitation on the scope of the technology, or on the claims that follow, is to be implied or inferred from the examples shown in the drawings and discussed here.

The present application discloses systems and methods for treatment of a variety of dermatological conditions using lasers, including systems providing a plurality of different wavelengths of laser light to provide improved therapies for certain skin conditions, with at least one of the wavelengths being determined by an optical parametric oscillator. In some embodiments, systems of the present disclosure permit rapid adjustment from a first treatment wavelength to a second treatment wavelength, at a range of wavelengths including visible wavelengths, near-infrared wavelengths, and mid-infrared wavelengths.

Embodiments of the invention involve systems and methods for one or more of treating a pigmentation condition in human skin (including without limitation removal of tattoos and benign pigmented lesions) and skin resurfacing (including without limitation treatment of acne and other scar tissue) using pulsed laser light having a high peak power (i.e., power per pulse). Multiple wavelengths of laser light suitable for use in such systems and methods are provided using an optical parametric oscillator (OPO).

In one aspect, a system capable of providing picosecond laser pulses at three or more different wavelengths suitable for treating pigmentation conditions and/or skin resurfacing is provided. In one aspect, a system capable of providing picosecond laser pulses at a plurality of wavelengths for treating pigmentation conditions and/or skin resurfacing using an OPO is provided. In one aspect, a system capable of providing high-energy, picosecond laser pulses at a plurality of wavelengths, including visible wavelengths and at least one of a near-infrared wavelength and a mid-infrared wavelength, is provided in a manner that allows a user to select one of the plurality of wavelengths quickly and easily.

In one aspect, a system capable of providing high-energy picosecond laser pulses at plurality of visible wavelengths and at least one of a near-infrared wavelength and a mid-infrared wavelength is provided in a manner that may be added to an existing picosecond laser system. In one aspect, a system for providing picosecond laser pulses at such wavelengths that is capable of long-term operation without loss of output energy or beam uniformity is provided. In one embodiment, the system is capable of provided more than 1 million laser pulses without significant loss of output energy or beam uniformity.

In one aspect, a tunable OPO capable of use in a dermatological picosecond laser system is provided that allows a user to select a desired wavelength within a range of 1700-2360 nm is provided, preferably a desired wavelength within one of a first range of 1700-1770 nm and a second range of 2280-2360 nm, more preferably a desired wavelength of about 1726 nm or about 2300 nm. In one aspect, a tunable OPO capable of use in a dermatological picosecond laser system is provided that allows a user to select a desired wavelength within a third range of 5900-9500 nm is provided, more preferably a desired wavelength of about 6049 nm or about 6476 nm. In one aspect, a tunable OPO capable of use in a dermatological picosecond laser system is provided that allows a user to select a desired wavelength within range of about 500-1200 nm, more preferably within one of a fourth range of from 1400-1850 nm, a fifth range of from 1910-1950 nm, and a sixth range of from 2600-3500 nm.

In one aspect, methods for providing a dermatological treatment according to one of the foregoing systems is provided.

FIG. 1 is a side view illustrating a cross-sectional view of a portion 100 of the skin of a patient, including the outermost epidermis 110, the middle layer or dermis 120, and the bottom layer or hypoderm is 130. The epidermis 110 has a thickness of about 80-100 µm, which may vary from patient to patient and depending on the area of the body. It includes up to five sub-layers and acts as an outer barrier. The outermost layer (the stratum corneum) consists of dead skin cells, which are constantly being replaced by new cells being made in the bottom layer (the stratum basale).

The dermal layer has thickness of about 1-5 mm (1000-1500 µm). The inks in a tattoo design and the melanin in a pigmented lesion are both located in the dermis. Consequently, laser light for removing tattoos and pigmented lesions must penetrate into the dermis. The dermis contains the blood vessels, nerves, hair follicles, collagen and sweat glands within the skin. Careful selection of a number of parameters must be made avoid damaging many of these structures in the design and construction of laser systems for removal of tattoos and pigmented lesions. For example, incorrect selection of the laser wavelength, pulse width, energy per pulse, the use (or nonuse) of a seed laser, or the pump energy of the laser source or amplifier may result in damage to one or more of the foregoing structures in the dermis, as well as poor performance in removal of the tattoo or pigmented lesion. Numerous other system choices, such as the use or non-use of an articulating arm for delivery of the laser light to a handpiece for application to the patient's skin, may also result in tissue damage and/or poor system performance if careful selection is not made.

The lowest layer of the skin is the hypodermis, which includes adipose tissue and collagen. The hypoderm is helps control body temperature by insulating the structures of the body below the skin. In addition, the hypoderm is protects the inner body tissues from damage by absorbing shock and impacts from outside the body. Because the hypoderm is contains fat, its thickness varies widely from person to person based on diet, genetic makeup, and other factors.

Figure 2:
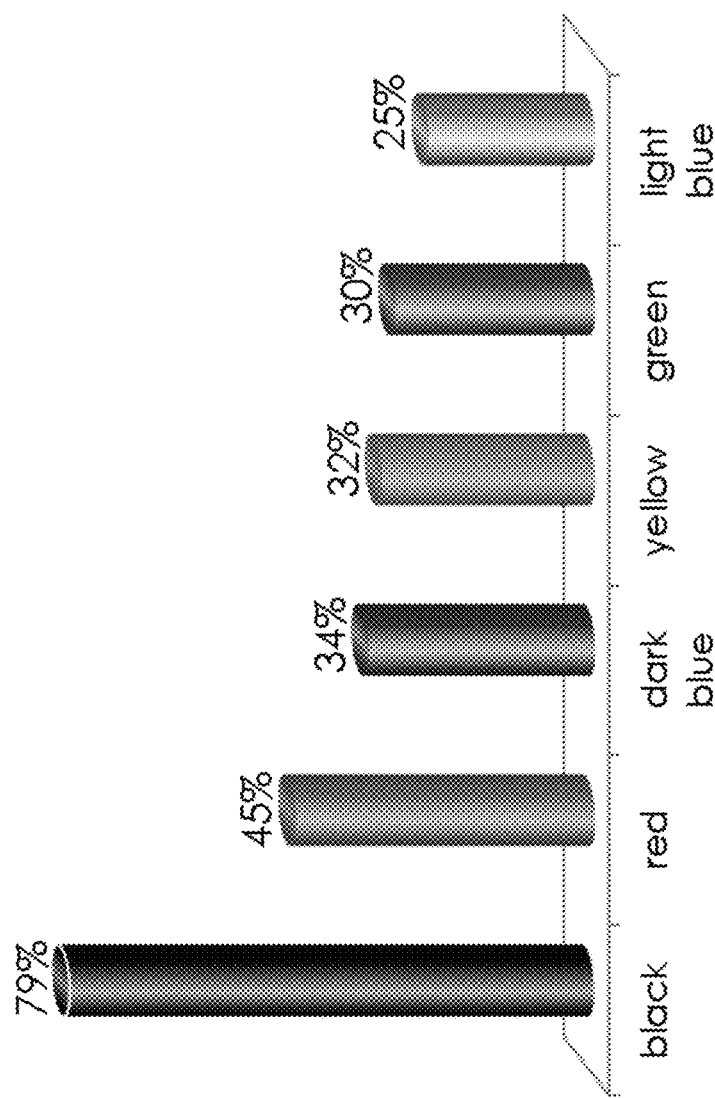
FIG. 2 is a graph illustrating the frequency of use of inks of various colors in tattoo designs.

FIG. 2 is a graph illustrating the frequency of ink use of certain colors in tattoo designs. Although black ink is the most frequently used color in tattoo designs (79% of tattoos), red ink is the next most frequently used color, appearing in about 45% of tattoo designs. Dark blue ink is used in about one third (34%) of tattoos, followed closely by yellow (32%) and green (30%) inks, respectively. Light blue ink is used in about one-fourth (25%) of tattoo designs.

Figure 3:
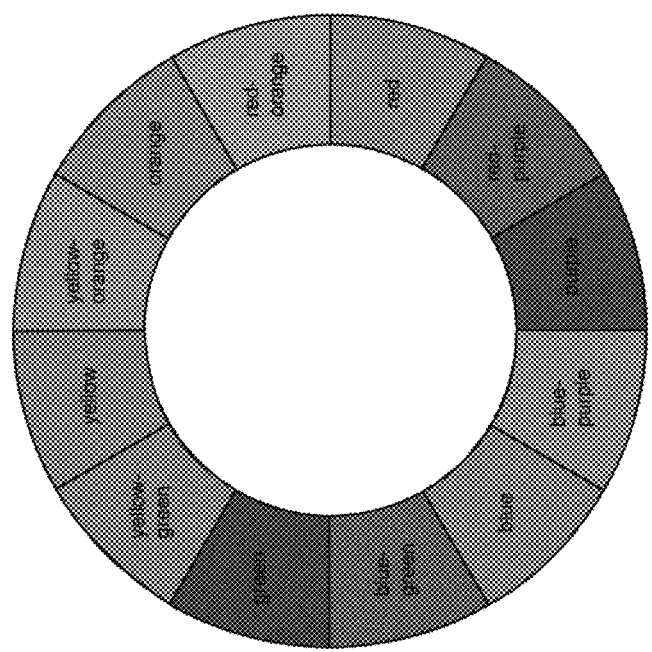
FIG. 3 is a color wheel illustrating various colors and their complementary colors.

FIG. 3 is a color wheel demonstrating the concept of complementary colors, which are the colors opposite to a given color on the color wheel. Thus, as previously noted, inks are more efficiently removed by laser light of a complementary color. Because of the prevalence of green and blue inks, it is desirable to have a system capable of reliably producing a red light wavelength in addition to the more widely available 1064 nm and 532 nm wavelengths.

The light absorbance profile of a substance is determined by the chromophores (i.e., the light-absorbing portions of molecules) within it that absorb light at particular wavelengths within the EMR spectrum. The color of a substance (e.g., skin) is determined by the absorbance profiles of the chromophores within the visible light portion of the EMR spectrum. Sunlight, although seen as a homogenous white color, is a composite of a range of different wavelengths of light in the ultraviolet (UV), visible, and infrared (IR) portions of the EMR spectrum. A substance appears to the eye as the complementary color of the light wavelengths that are absorbed.

Laser-based removal of pigmentation occurs by applying light at high fluences (i.e., energy per unit area) such that the chromophore-containing compounds within the pigmented area (e.g., ink particles in a tattoo or melanin in freckles or age spots) absorb so much energy that the ink or melanin particles in the pigmented area are ruptured or broken into small particles that may be removed by the body.

The more highly absorbed the wavelength of laser light by melanin (in the case of pigmented lesions) and/or inks (in the case of tattoos), the more efficient the removal. Stated differently, less energy must be delivered to rupture an ink or melanin particle if the wavelength of the laser light being used is highly absorbed by the ink in the tattoo or the melanin in the pigmented lesion. The absorption profile is only one aspect of laser wavelength selection, however, and a wide range of laser wavelengths are used to remove tattoos and pigmented lesions, including wavelengths in the visible and near-IR spectrum. Commercially available systems for removal of tattoos and pigmented lesions have used laser light at 532 nm, 597 nm, 650 nm, 755 nm, 785 nm, and 1064 nm, among others.

Figure 4:
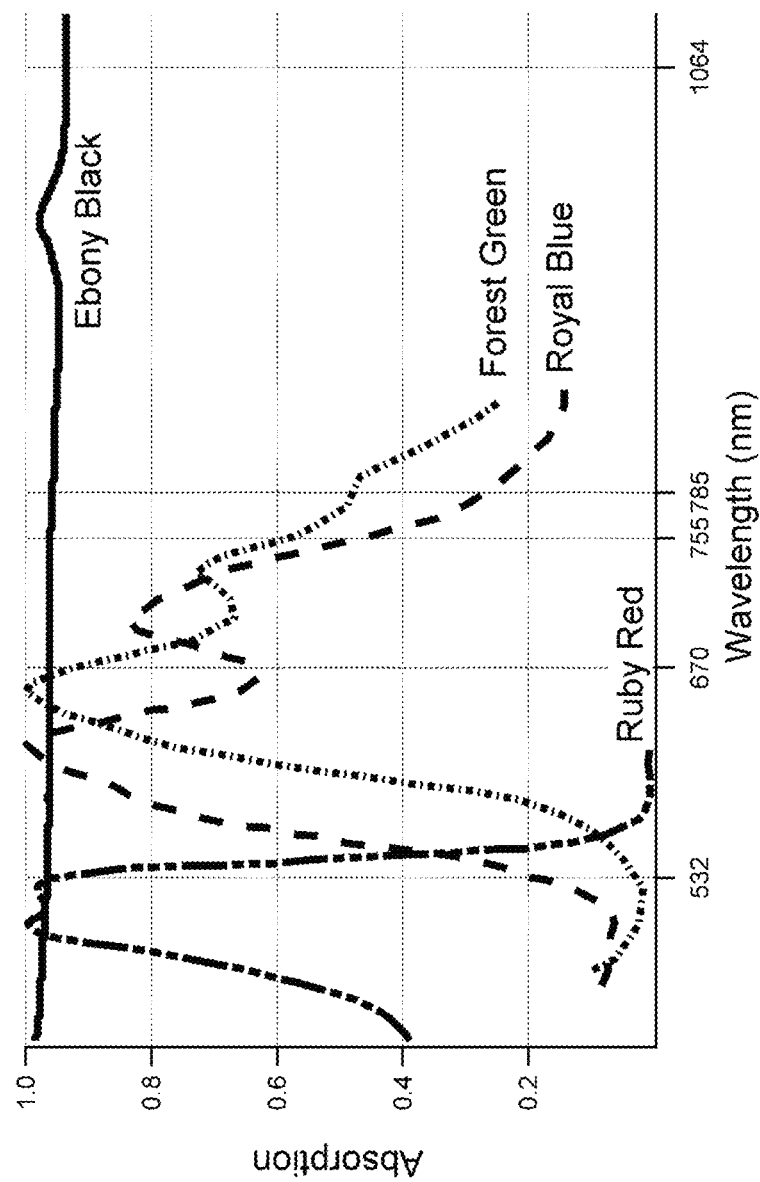
FIG. 4 is a graph illustrating the absorption spectra of red, green, blue, and black ink for various wavelengths of light.

FIG. 4 is a graph illustrating the absorption curves for various tattoo ink colors at a range of wavelengths. As previously noted, black ink ("ebony black") has a high absorbance across a wide range of laser wavelengths. Accordingly, black ink in tattoos may be efficiently removed using a variety of different laser systems and wavelengths.

FIG. 4 also shows that red ink ("ruby red") has a high absorbance at 532 nm and nearby wavelengths, but its absorbance falls rapidly at higher wavelengths. Consistent with the concept of complementary colors discussed earlier, the 532 nm wavelength corresponds with green light in the visible spectrum, which is the complementary color of red. Accordingly, red light may be removed efficiently by 532 nm green laser light but is poorly removed by, for example, 670 nm light in the red light portion of the visible spectrum.

Conversely, FIG. 4 shows that green ink ("forest green") has a high absorbance of 660-670 nm red light. Thus, tattoos with green ink are much more effectively removed by 660-670 nm laser light that, for example 532 nm green light, which is very poorly absorbed by green ink. Although green ink has a reasonable absorbance of near-infrared light at 755 and 785 nm (absorbance of about 0.6 and 0.5, respectively), it has more than 50% greater absorbance at 660-670 nm wavelengths (absorbance >0.9) in the visible red portion of the spectrum. Accordingly, 660-670 nm red laser light may provide for removal of green inks in tattoos with reduced laser intensity or fluence, fewer treatments sessions, or both, than green or near-infrared wavelengths.

FIG. 4 also illustrates that 660-670 nm red light will more efficiently remove blue inks ("royal blue") than near-infrared wavelengths such as 755 and 785 nm. Although not as strongly absorbing of red light as green inks, blue inks similarly show a much stronger absorption at a 670 nm wavelength than at 755 and 785 nm near-infrared (~40% greater absorbance than 755 nm wavelength and ~50% greater absorbance than 785 nm wavelength). Accordingly, 660-670 nm red light offers improved removal of blue inks than current widely used wavelengths.

Figure 5A:
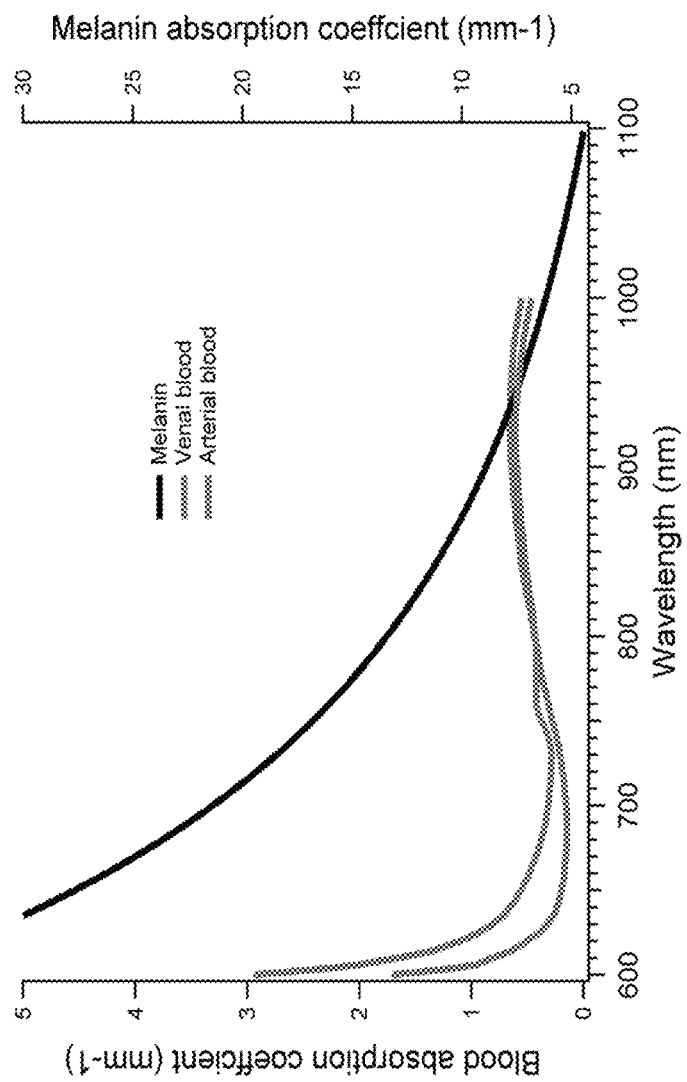
FIG. 5A is a graph illustrating the absorption coefficients of melanin, venous blood, and arterial blood for various wavelengths of light.

FIG. 5A is a graph illustrating the absorption curves for venal and arterial blood and melanin at various wavelengths of light. For removal of pigmented lesions, it is desirable to target melanin in the skin to the exclusion of other structures, notably blood and blood vessels. Greater safety may be provided by wavelengths that are poorly absorbed by non-target structures. FIG. 5A illustrates that melanin is strongly absorbent at lower wavelengths of light in the red visible wavelengths around 650, but its absorbance decreases steadily to a very low absorption in the near-infrared region. The absorbance of venous and arterial blood, on the other hand, decrease rapidly from 600 nm through about 650 nm. Arterial blood (lower curve) decreases rapidly until a relatively flat absorbance profile in the range of 630-700 nm, with a minimum value around 680 nm. Venous blood decreases rapidly to about 630-640 nm, then decreases more slowly to a minimum value at around 730 nm.

Maximum safety margin is provided at wavelengths having the maximum distance between the absorption curves of melanin on the one hand and venous/arterial blood on the other. This occurs between about 670 nm and about 700 nm, indicating that red laser light in this range will minimize damage to blood and blood vessels in the treatment of pigmented lesions. Thus, it would be desirable to add a red laser light capability to existing 1064/532 nm dermatological systems.

Figure 5B:
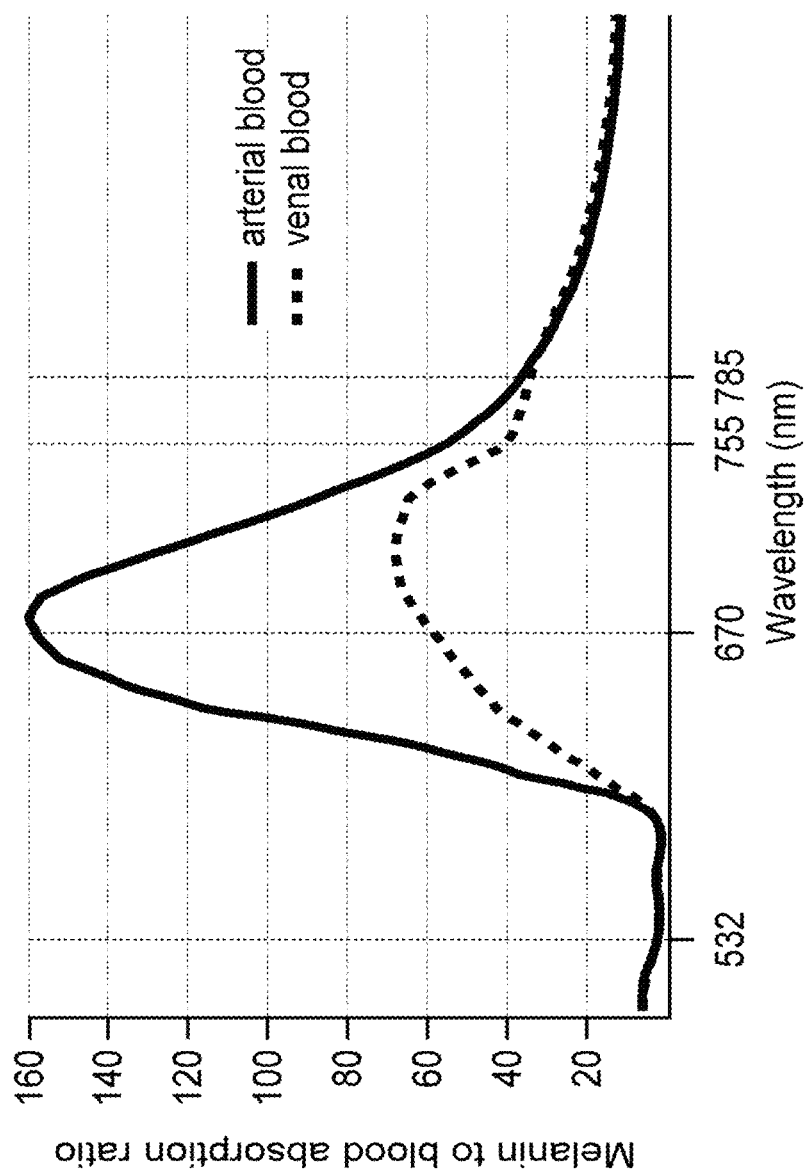
FIG. 5B is a graph illustrating the melanin to blood absorption ratio for venous and arterial blood for various wavelengths of light.

FIG. 5B illustrates this in another way by graphically indicating the ratio of the absorption ratios of venous and arterial blood to melanin. As the arterial blood curve demonstrates, melanin has its maximum absorption relative to arterial blood at a wavelength slightly above 670 nm. For venous blood, melanin reaches its relative peak at about 700 nm. Accordingly, red light in the 670-700 nm range, in addition to providing improved removal of green and blue tattoo inks, also offers potentially greater safety in removal of pigmented lesions.

In one embodiment, systems of the present invention may provide pulsed laser light at one or more wavelengths selected for efficient removal of tattoos having a wide range of ink densities. In one embodiment, a user may select a wavelength within a desired range for at least a portion of the wavelength output range that the system is capable of producing. In one embodiment, the laser pulses of the system have a pulse energy ranging from 100-1500 mJ/pulse. In one embodiment, the laser pulses of the system have a peak power of 250 megawatt (MW) or higher, preferably 500 MW or higher, more preferably 1 GW or higher. In one embodiment, a dermatological treatment system provides laser light at a fluence of up to 5.0 J/cm$^2$. In one embodiment, a user may select a spot size (e.g., by adjusting the diameter of a laser beam) for treating a pigmentation condition.

Some embodiments of the present invention involve high-energy pulsed lasers and an optical parameter oscillator (OPO) to provide a variety of selectable wavelengths for one or more of treatment of pigmentation conditions and skin resurfacing. Applicants have discovered that OPOs may be used to generate a range of pulsed laser wavelengths useful in removal of tattoos and benign pigmented lesions. Producing of such wavelengths using an OPO, however, requires a laser capable of producing relatively high-energy pulses. As used herein, the term "laser engine" refers to a pulsed laser system capable of producing pulses having a peak power of 250 megawatt (MW) or higher, preferably 500 MW or higher, more preferably 1 GW or higher.

Figure 6:
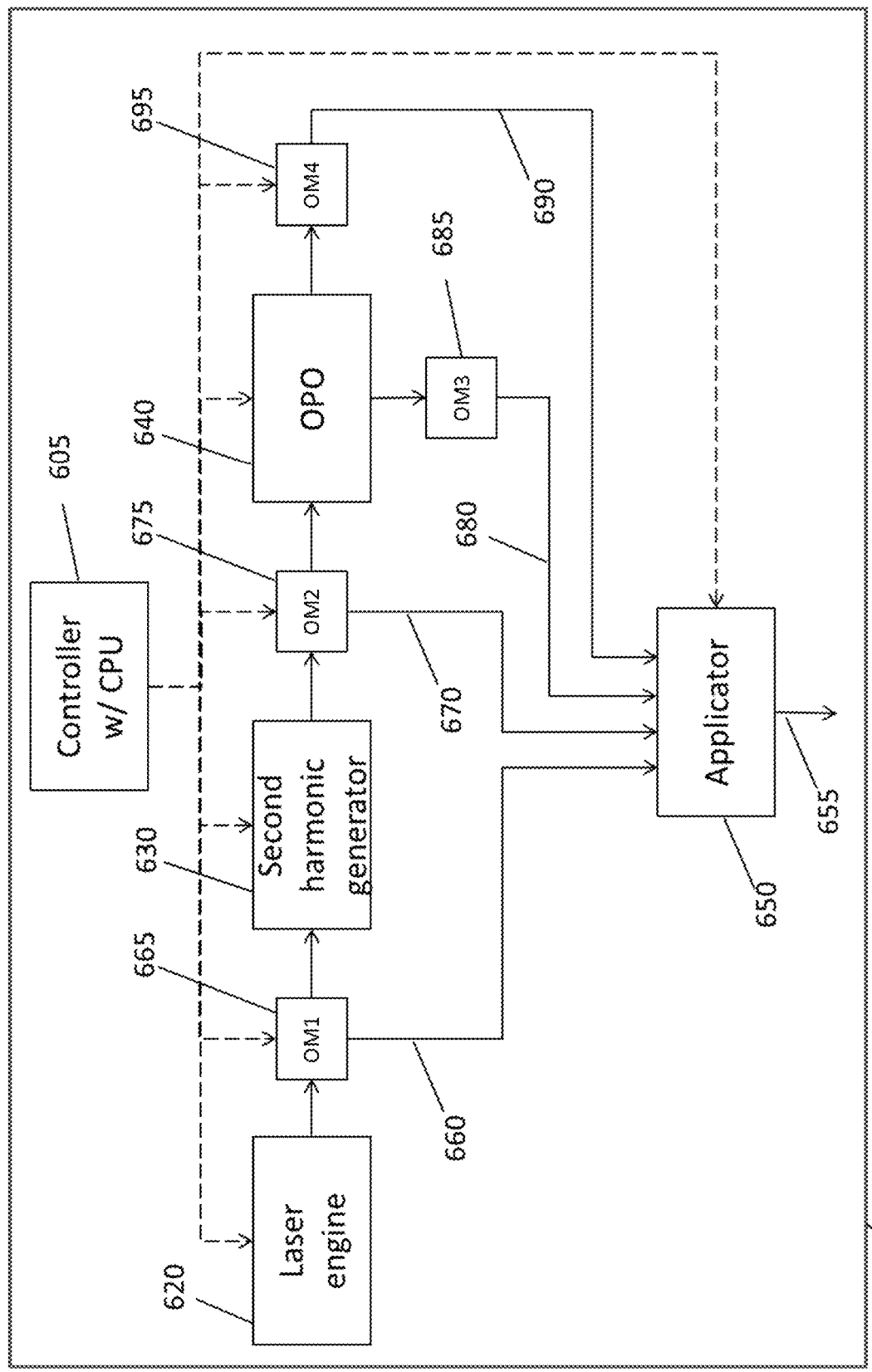
FIG. 6 is a block diagram of a system for treatment of dermatological tissue using pulsed laser light according to one embodiment of the present disclosure.

FIG. 6 is a schematic illustration, in block diagram form, of a dermatological laser treatment system 600 using high-energy pulsed laser light according to the present disclosure. A laser engine 620 is provided to produce high-energy pulsed laser light at a desired wavelength. Although a number of different laser engines are described in the present disclosure, the description herein of certain laser engines should not be construed as excluding others not specifically described. It will be appreciated by persons of skill in the art in view of the present disclosure that a variety of different materials, designs and techniques may be employed to generate high-energy pulsed laser light in systems of the present invention. Unless specifically excluded by the scope of the claims, all are considered to be within the scope of the present disclosure.

Laser engine 620 outputs laser pulses having a wavelength of from 1000 nm to 1200 nm, a pulse width (PW) of 10 psec to 10 nsec, and a pulse energy (PE) of 100 mJ/pulse to 5 J/pulse. In view of the fact that the peak power is given by the pulse energy divided by the pulse power or PE/PW, it will be appreciated that a variety of pulse widths and pulse energies may be used to produced high-energy laser pulses at a desired wavelength and having a peak power of 250 megawatt (MW) or higher. In one embodiment, laser engine 620 is a Q-switched laser.

A second harmonic generator (SHG) 630 receives the laser pulses from the laser engine 620 and generates second harmonic laser pulses with a wavelength that is half that of the pulses received from the laser engine 620. Many different crystals may be used for SHG, which results in an output signal having double the frequency and half the wavelength of the pumping signal. In the case of 1064 nm (fundamental) and 532 nm (second harmonic) wavelengths, potassium titanyl phosphate (KTP) and lithium tetraborate (LBO) are common choices, although other crystals such as potassium dihydrogen phosphate (KDP) may also be used. The crystals typically have a length between 2 and 15 mm. Depending on which material is chosen, the laser engine pulses received by the SHG may not require focusing to achieve efficient conversion to the second harmonic.

An optical parametric oscillator (OPO) 640 receives the pulses from the SHG and provides two pulsed laser outputs, known as the "signal" and "idler" respectively. Both OPO outputs (i.e., the OPO signal pulses and the OPO idler pulses) comprise laser light having a wavelength longer than the light received from the SHG 630. Optical parameter oscillators operate by receiving a pump laser signal (e.g., pulses as a first wavelength), which is used to induce parametric amplification within a nonlinear crystal in the OPO to produce the two output electromagnetic fields (i.e., the OPO signal pulses and the OPO idler pulses). OPOs are tunable over a wide range of wavelengths and potentially offer the ability to produce any desired wavelength within a range of desired wavelengths.

An applicator 650 is provided to receive pulsed laser light 655 from one or more of the laser engine 620, the SHG 630, and the OPO 640, and apply the received laser pulses to the skin of a patient for treating a pigmentation condition or skin resurfacing. The applicator may comprise a handpiece adapted to be held in the hand of a user, such as a physician or other healthcare provider, for treating the patient with pulsed laser light 655.

In some embodiments, the applicator may also comprise a selector (e.g., a touchscreen on the applicator) allowing a user to select the pulses from one or more of the laser engine 620, the SHG 630, the OPO (640) signal, and the OPO (640) idler for application to the skin of the patient. A first output path 660 is provided to direct the output of laser engine 620 to the applicator 650. In the embodiment of FIG. 6, first output path 660 comprises an optical multiplexer 665 between the laser engine 620 and the SHG 630 to direct the laser pulses from laser engine 620 to the applicator 650. A second output path 670 is provided to direct the output of the SHG 630 to applicator 650. In the embodiment of FIG. 6, an optical multiplexer 675 located between the SHG 630 and the OPO 640 directs the pulsed SHG output to the applicator 650. A third output path 680 is provided to direct the OPO signal output to the applicator 650. In the embodiment of FIG. 6, an optical multiplexer 685 located at the OPO signal output directs the OPO signal pulses to the applicator 650. In some embodiments, as shown in FIG. 6, a fourth output path 690 is provided to direct the OPO idler output pulses to the applicator 650. In the embodiment of FIG. 6, an optical multiplexer 695 located at the OPO idler output directs the idler output pulses to the applicator 650. In some embodiments, optical multiplexer 695 is omitted. In some embodiments (not shown) a single optical multiplexer and output path may be provided for both the OPO signal pulses and the OPO idler pulses.

In some embodiments, one or more of optical multiplexers 665, 675, 685, and 695 may be selectable by a user, e.g., by a rotatable mirror (not shown) from an interface located on the applicator 650, to allow the user to choose one among a plurality of available wavelengths of light to be routed to the applicator 650 to treat a patient. In addition, although the embodiment of FIG. 6 illustrates each of the first, second, third and fourth output paths, in alterative embodiments (not shown), one, two, or three of the four output paths shown may be omitted, such that pulses for one or more of the laser engine 620, the SHG 639, and the OPO 649 may not be available to treat a user. Although not shown in FIG. 6, one or more beam dumps may also be selectable by a user to shunt the laser pulses from one or more of the laser engine 620, the SHG 630, the OPO 640 signal output pulses, or the OPO 640 idler output pulses.

Although laser systems according to FIG. 6 may be constructed in a number of different physical layouts, a housing or chassis (not shown) may be used to provide store and protect some or all of the foregoing optical components. In one embodiment (not shown) a movable console (e.g., a wheeled cart) may function as a housing to house the laser engine 620, the SHG 630, the OPO 640, and the optical multiplexers 665, 675, 685, and 695. In one embodiment, an articulated arm having an optical medium (e.g., one or more waveguides) therein may be used to provide an optical path for the optical multiplexers 665, 675, 685, and 695 to direct pulses for a selected one of the laser engine 620, the SHG 630, the OPO 640 signal output, and the OPO 640 idler output pulses to the applicator (e.g., to a handpiece constructed and arranged to be held in the hand of a user). In one embodiment, a movable console may be provided as a housing to house the laser engine 620, SHG, and optical multiplexers 665 and 675, with the OPO 640 and optical multiplexers 685 and/or 695 located in an applicator such as a handpiece.

Finally, a controller 605 is provided, together with appropriate electrical circuitry, to control the operation of the dermatological laser treatment system of FIG. 6. In one embodiment, the controller 605 controls the operations, including the electrical operations, of one or more (and preferably all or most) of the laser engine 620, the SHG 630, the OPO 64, and applicator 650. In one embodiment, the controller 605 controls the operations of one or more of the laser engine 620, the SHG 630, the OPO 640, and multiplexers 665, 675, 685 and 695.

Laser engine 620 may comprise any of a number of designs to achieve stable, high-energy pulses, and all such designs are intended to be within the scope of the invention. In one embodiment (not shown), laser engine 620 comprises a seed laser providing a pulsed initial laser signal for further amplification by an amplifier. Seed lasers are frequently used to produce a low power initial signal that may be amplified to obtain a final laser signal having desired characteristic. Many characteristics that may be desired in the final signal (e.g., short pulse widths, a wavelength having a narrow spectral line width) are easier to produce in a seed laser than in a single, high-power laser. The seed laser signal may then be easily amplified to obtain a laser signal having desired characteristics.

Although many seed lasers produce pulses having a pulse energy of 1 µJ or less, in one embodiment, a high-power seed laser is provided. The high-power seed laser is capable of producing pulses of at least 100 µJ per pulse, more preferably 100 µJ to 10 mJ, with a narrow linewidth and a wavelength of from 900-1200 nm, as well as a pulse width of 1 psec to 100 nsec. In one embodiment, the seed laser produces pulses having a stable polarity, and may be constructed and arranged to produce other desirable characteristics to enable the amplifier to output high-energy output pulses having a pulse energy of 100 mJ to 5 J, more preferably 500 mJ to 5 J, a wavelength of 1000-1200 nm, and a pulse width of 200 psec to 10 nsec. The pulses in seed laser have a relatively high peak power that may be amplified to obtain high-energy pulses as required by laser engine 620. In various embodiments, the seed laser may take the form of many oscillators known in the art to produce picosecond pulses including fiber lasers, microlasers, or diode lasers.

The pulsed output of the seed laser is received by an amplifier (not shown), which amplifies the output of the seed laser to produce amplified laser light having the same pulse width and wavelength as the seed laser, but with a greater pulse energy. In one embodiment, the amplifier amplifies the seed laser pulses by a factor of 1000 or more. The amplified laser pulses output from the amplifier may, in some embodiments, be output (e.g., to an applicator such as applicator 650) and used to treat a dermatological condition of a patient. Multiple approaches in the art are known for amplifiers that will amplify laser signals to a pulse energy of >100 mJ, including >500 mJ.

In one embodiment (not shown), laser engine 620 may comprise a high power oscillator. In one embodiment (not shown), laser engine 620 may comprise a hybrid mod-elocked laser combining the functions of a laser oscillator and amplifier into a single cavity. Other approaches may also be used to produce appropriate laser engines 620.

There are a number of challenges to producing an OPO capable of pulse energies of 50 mJ/pulse or greater for picosecond lasers. For optimized designs, the conversion efficiency of pump light to output (signal and idler) is about 30-50%. Because of the high energies involved, relatively large beam diameters must be used to avoid exceeding the threshold intensity to damage to optical structures within the OPO. In addition, the cavity length must be limited to enable the light to make at least 10-30 round trips across the cavity during the pulse duration (or width) to enable the signal and idler fields to build up to maximum energy. This results in a scaling law of about 1 cm/ns for the maximum cavity length vs. pump pulse duration. Thus, for a nanosecond laser having a pulse duration of 5 ns, the cavity length should be limited to 5 cm or less. For a picosecond pulse, the cavity length should thus be limited to less than 1 cm. However, it is not possible to simply make the cavity very small because cavity length is inversely related to beam quality, as explained below.

The combined constraints of large beam diameter and short cavity length imposed for achieving high pulse energies (50 mJ/pulse or greater) for picosecond pulses creates a fundamental challenge for OPO performance, because they result in the cavity having a high Fresnel number, expressed as $N=d^2/(4L\lambda)$, where N, d, L, and $\lambda$ are Fresnel number, beam diameter, cavity length and wavelength, respectively. Thus, because the Fresnel number varies inversely with the cavity length L, the smaller the cavity length, the larger the Fresnel number. It is well-known that optical cavities with $N \gg 1$ are prone to lasing many transverse optical modes, and therefore have low beam quality.

Beam quality in laser systems is typically expressed as $M^2$, which provides a measure of the spatial coherence of the beam and therefore how well it can maintain collimation over a given distance. The larger the value of $M^2$, the higher the divergence angle of the beam (i.e., lower values indicate higher beam quality). The $M^2$ parameter is a critical measure for laser emission because it impacts the complexity of the optical delivery system design. For high energy picosecond medical laser systems requiring an articulated arm to deliver the beam to the applicator (e.g. a handpiece), the larger the value of $M^2$, the larger the diameter of the arm required to accommodate the divergence associated with the deterioration of the beam quality.

Figure 7:
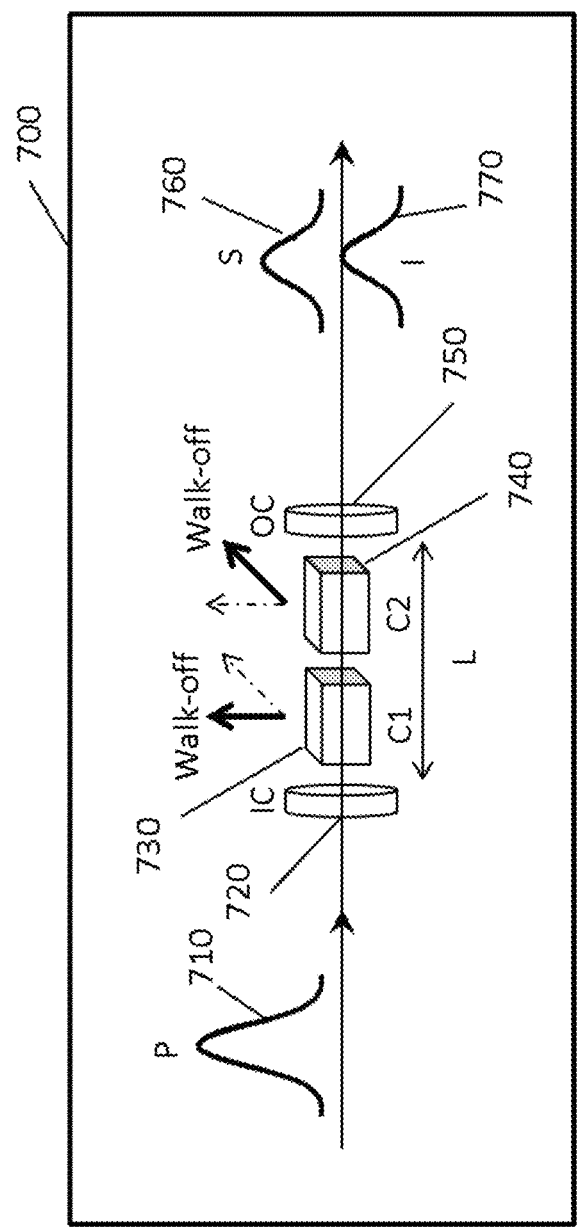
FIG. 7 is a block diagram of a prior art optical parametric oscillator suitable for use in dermatological treatment systems with nanosecond lasers.

An example of a proposed OPO design illustrates the problem. In an OPO design proposed by Rustad et al. (FIG. 7) loss of beam quality was addressed by using two non-linear crystals C1 (730) and C2 (740) with orthogonally oriented beam walk-off axes and tuning of the signal wavelength to 670 nm to induce absorption of the idler pulses 770 in one of the crystals. The Rustad design proposes a 5 nsec pulse 710 having an input pulse energy of 120 mJ, a beam diameter of 6 mm, and a pulse wavelength of 532 nm. An input coupler mirror 720 is highly reflective (HR) at the 670 nm OPO signal wavelength and highly transmissive (HT) at the 532 nm pump or input wavelength. An output coupler 750 has high reflectance (HR) at the 532 nm pump wavelength and 35% reflectance at the 670 nm OPO signal wavelength, outputting OPO signal pulses 760 having a pulse energy of approximately 50 mJ. OPO 700 also produces idler pulses 770, shown in FIG. 7 for illustration as being output from output coupler 750 but which were, according to Rustad et al., absorbed within nonlinear crystals 730 and/or 740.

In simulations, Rustad et al. demonstrated that walk-off in orthogonal axes and absorption of the idler signal within the crystals 730, 740 may be combined to achieve a beam quality parameter $M^2 \approx 2$. Without idler absorption, the beam quality decreased to $M^2 \approx 8$. They also determined that the maximum efficiency is achieved when both crystals were 20 mm long. The cavity had a Fresnel number of N=335, indicating that the Rustad design significantly improved expected beam quality.

However, the Rustad et al. design is not well suited to use in picosecond laser systems. Applying the foregoing scaling law for a 750 psec pulse, the cavity is limited to less than 1 cm (about 0.75 cm in length), which is insufficient length to provide two nonlinear crystals of adequate length. More significantly, a 750 psec pulse increases the peak power of the pulse by a factor of 6 compared to a 5 nsec (5,000 psec) pulse. Thus, to keep the fluence the same and avoid damaging the optical components of the OPO, the beam area must also be increased by a factor of 6.6 and the beam diameter by a factor of 2.6. This would result in a cavity Fresnel number of N=9080 and a beam quality of $M^2 > 500$.

The present applicants have developed an OPO usable in picosecond laser systems that is adapted to overcome the limitations of conventional designs while maintaining high beam quality.

In one aspect, the present disclosure provides a tunable OPO capable of providing tunable emission wavelengths from visible to infrared for use in a dermatological laser treatment system. The first optical parametrical oscillator was developed in 1965 at Bell Labs. OPOs use a nonlinear optical crystal pumped by a laser pulse to produce simultaneous emission at a signal wavelength and an idler wavelength. The signal and idler wavelengths may be tuned throughout a range of wavelengths by adjusting either the crystal temperature or its angle of incidence with respect to the laser pump beam. OPOs may be designed with the signal and idler wavelengths in the visible and infrared spectral range.

Although high-energy pulsed OPOs have been long recognized as capable of producing optical emission over a broad spectral range, their commercial application to date has been limited, primarily because the conversion of pump emission to the signal and idler wavelengths proceeds by a non-linear process and is inefficient unless the pump pulse has a very high peak power, on the scale of 1 GW. Because of the cost and size, GW-level pulsed laser sources have not been commercially viable. In addition, the overall system complexity typically requires optical elements to be periodically realigned. Because of these factors, OPOs have until very recently been limited been limited to scientific instruments that require periodic tuning by the user. There is a need in the medical field for improved pulsed laser systems using OPOs to produce tunable emission at multiple spectral ranges, and a compact, simplified laser pump engine producing laser pulses with pulse energies on the order of 1 J and peak powers of approximately 1 GW.

Scientific lasers producing such output levels typically use a master oscillator power amplifier (MOPA) configuration in which a simple and compact oscillator produces a low-energy seed laser pulse that is then amplified to a final pulse energy in an amplifier. Common compact seed oscillators include diode and fiber lasers with pulse energies in the 1 nanojoule (nJ) to 100 microjoule (µJ) range. Since the gain of most optical amplifiers is limited to 10 to 100 because of parasitic effects such as amplified spontaneous emission (ASE), a complex series of amplifiers are needed to amplify the seed pulse to 1 J.

In one embodiment, the OPO is pumped by a pulsed laser engine using a microlaser oscillator to produce the seed pulse. Microlasers are very compact (approximately 1 cm long), passively Q-switched lasers that have been demonstrated to produce pulse energies up to 1 mJ with pulse durations of 200-1000 psec. The main elements of a microlaser include a high reflectance (HR) mirror, a laser gain crystal, a saturable absorber (passive Q-switch), and an output coupler. Since the peak power can be on the order of 2 MW (=1 mJ/500 psec), which is 10 to 100,000 times higher than common seed lasers, the number of amplifiers and thus the complexity of the amplifier design can be reduced dramatically.

However, high-energy (>100 µJ) microlasers have notoriously poor pulse energies and spatial beam quality. To achieve high pulse energy, a large mode size (approximately 500 µm diameter) must be used. Because of the short (approximately 1 cm) cavity length, this results in a cavity with a high Fresnel number that is very sensitive to optical misalignment. To overcome this, some embodiments use a monolithic microlaser in which the components are permanently bonded together such that misalignment is not possible.

Another complication of microlasers is their tendency to produce laser emission with unstable polarization properties. Any polarization instability in the microlaser output will be carried through to the final output of the amplifier. Conversion of pump energy to signal and idler wavelengths in an OPO is sensitive to the pump polarization, so it is important in embodiments of the present invention for the microlaser to have stable output polarization to be used as the seed laser for the laser engine to pump the OPO. Because of the short microlaser cavity length, integration of common polarization controlling intra-cavity optical elements such as polarizers and Brewster plates is not practical. Thus, in some embodiments, the present invention incorporates a grating waveguide mirror (GWM) for the microlaser output coupler to control its output polarization.

In some embodiments, both the fundamental wavelength of the amplifier emission as well as its second harmonic can be used to pump the OPO. In general, the tuning ranges of the OPO signal and idler wavelengths depend on the pump wavelength. Having multiple pump wavelengths available from the same pump engine can expand the total available spectral coverage from one or more OPOs. For example, if Nd:YAG is used as the laser material for the laser pump, the 1064 nm emission could be used to pump an OPO directly, or it could also be used to produce 532 nm light that is subsequently used to pump an OPO. Thus, in some embodiments, the second harmonic of the laser engine wavelength is obtained by second harmonic generation (SHG) in a nonlinear crystal.

In some embodiments, OPO-based systems of the present disclosure are capable of producing a wide range of temporal pulse formats. As previously noted, one of the requirements for achieving selective photothermolysis of a target tissue is that the laser pulse duration must be smaller than the thermal relaxation time of the target tissue. In fact, the pulse duration is typically set to 50 to 100% of the thermal relaxation time since further shortening does not significantly improve thermal confinement of the absorbed laser energy in the target but can limit the maximum fluence that can be used.

In some embodiments, the laser engine of the dermatological treatment system may be adapted to operate in one of a first treatment mode or a second treatment mode. In the first treatment mode, which may be referred to as "pulse mode," the laser engine outputs individual pulses at a pulse frequency of from 0.1 Hz to 100 Hz. Such pulse formats may be used on tissues with short thermal relaxation times (TRTs). In the second treatment mode, which may be referred to as "burst mode," the laser engine outputs a plurality bursts at a burst frequency of 1 Hz to 100 Hz. Each burst comprises a plurality of individual pulses, with the pulses within the burst having a pulse frequency greater than 100 Hz, and preferably greater than 1000 Hz. Each burst is characterized by a burst duration of from 500 μsec to 50 msec, a burst energy of from 10 mJ to 20. In some embodiments, a user interface may be provided by which the user may select the laser engine to operate in pulse mode or in burst mode. The user may also specify one or more of the foregoing parameters defining the pulse mode (e.g., pulse frequency) or burst mode (e.g., burst frequency, pulse frequency within the burst, burst duration, burst energy, etc.), and may also select one or more laser engine parameters.

For example, when treating tattoos, the user may select pulse mode operation, and may specify a 750 psec pulse duration with a pulse frequency between 1 and 10 Hz. In this case, the microlaser is simply driven at the desired pulse frequency with each 750 psec pulse amplified and acting as an individual treatment pulse. However, when treating blood vessels, which have a longer TRT than tattoo ink particles, it may be desirable to have a longer pulse duration, which may be from about 1-10 msec. In this case, the user may select burst mode operation to produce a 1-10 msec long burst of pulses at high repetition rate (e.g., individual pulse rate of 10,000 Hz). If the pulse duration is much shorter than 10 msec, the burst will appear to the tissue like a continuous 10 msec pulse. Because microlasers have such a short cavity length, the pulse build-up time is short and therefore they are well suited for operation at high repetition rates.

In one aspect, the present disclosure provides dermatological treatment systems incorporating multiple OPOs that are each tuned (or are tunable by a user) to different wavelengths within a selected range of wavelengths to provide a wide range of spectral coverage. In some embodiments, the laser engine is located within a housing, which may also enclose various optical multiplexers and power sources, etc. The laser pulses may be applied to the tissue of a patient using an applicator that may comprise a handpiece adapted to be held in the hand of a user such as a physician or technician.

In some embodiments, the OPOs may be located in the housing while in other embodiments the OPOs may be located within the applicator. In still other embodiments, some OPOs may be located in the housing and some OPOs may be located within the applicator. In some embodiments, a plurality of applicators, each having an OPO that is tunable within a specific range of wavelengths, may be attachable to and detachable from the laser engine and/or an SHG output to provide pulse mode or burst mode delivery of therapy to a target tissue. In one embodiment, an articulating arm may be used to couple the one or more handpieces to the laser engine and/or SHG. One advantage of such an approach is that a user may purchase OPO-containing handpieces as an accessory and the system may be a modular, expandable system.

Figure 8:
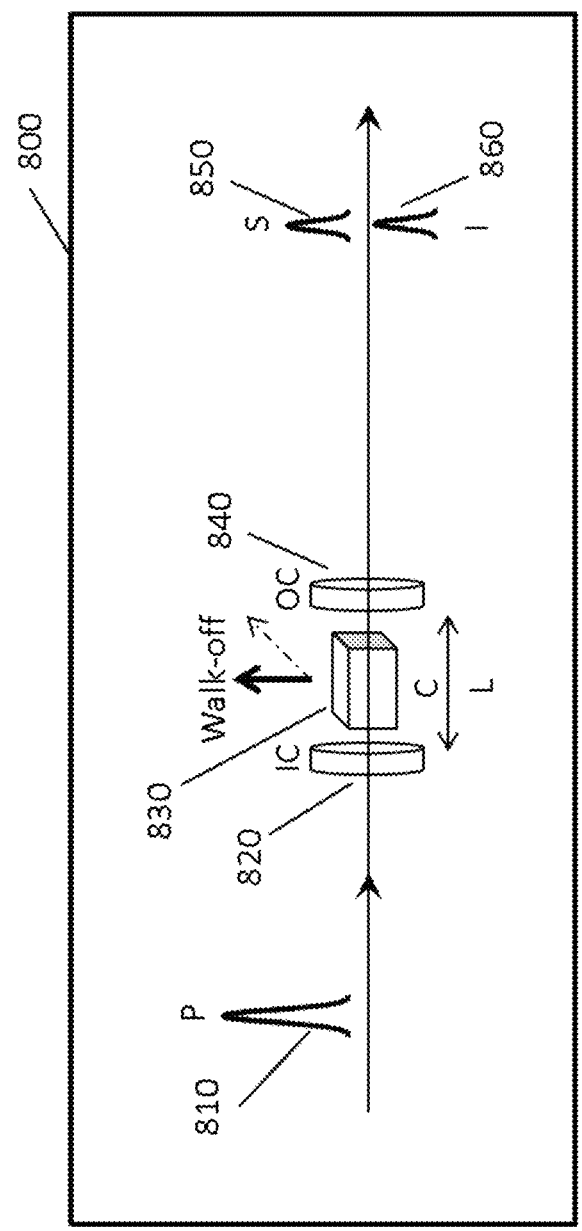
FIG. 8 is a diagram of one embodiment of an OPO of the present invention.

FIG. 8 is a schematic view of the optical elements of an optical parametric oscillator 800 according to one embodiment of the present invention. The OPO is adapted to be used in dermatological laser treatment systems having pulse energies of 50 mJ/pulse or higher. A pump laser providing pulses 810 is used to induce parametric amplification within a nonlinear crystal 830 to produce OPO signal pulses 840 and OPO idler pulses 850. The wavelengths of both the OPO signal pulses 840 and the OPO idler pulses 850 may be adjusted (or tuned) to achieve a desired wavelength with a wide range of possible wavelengths. Adjustments may be made, in different embodiments, by alteration of the crystal orientation (e.g., angle relative to the optical axis) or temperature.

For dermatological applications the ability to selectively damage target tissues or tissue structures is strongly determined by laser wavelength. Accordingly, embodiments according to the present disclosure offer the potential to select a desired wavelength within a wide range of available wavelengths to obtain the optimum wavelength for a particular target tissue or structure, in stark contrast to current dermatological approaches where the available wavelengths are limited to the atomic emission lines of the laser material being used and its harmonic wavelengths.

As already noted in connection with FIG. 6, in various embodiments of the invention the OPO 800 may be located in a console or housing, or in an applicator such as a handpiece. In some embodiments, the OPO 800 is located in the console or housing to enable wavelengths to be rapidly changed by a user and to enable the use of an articulated arm to deliver any of the available wavelengths to a single handpiece. The dimensions of typical articulated arms are about 15-20 mm ID and 1.5 meter length, and require a beam to have a beam quality of $M^2 \sim 100$ to avoid clipping the beam (because of beam divergence) inside the articulated arm. Accordingly, it is necessary to improve beam quality from $M^2 > 500$ to $M^2 \sim 100$, without relying on multiple crystals or extending the cavity length beyond 10 mm.

The present invention provides those results in a single-crystal design that, contrary to prior designs, enables absorption of the OPO idler pulse wavelength within the OPO crystal to improve beam quality sufficiently to enable delivery through an articulated arm.

Referring again to FIG. 8, in one embodiment, nonlinear crystal 830 comprises a BBO (beta barium borate) crystal positioned between a pair of flat mirrors 820, 840 defining the OPO optical cavity. In one embodiment, a first mirror

820 serves as an input coupler and has high transmission (HT) at 532 nm and is highly reflective (HR) at the OPO signal wavelength, which in various embodiments may range from 575-750 nm, 620-720 nm, 660-680 nm, and about 670 nm. A second mirror 840 serves as an output coupler and transmits a portion of the signal wavelength. Second mirror 840 may be constructed to achieve a desired signal transmission from, e.g., 10-99%, preferably 25-75%, more preferably 40-60%, more preferably about 50%. The pump pulse width (or duration) may range from 1 psec to 1 nsec, preferably 100 psec to <1 nsec, more preferably 500-750 psec. In various embodiments, nonlinear crystal 830 may have a length of 5-25 mm, preferably 5-15 mm, and more preferably about 10 mm. In one embodiment, the pump beam has a diameter between 4 and 15 mm, more preferably about 10 mm.

The OPO 800 may have an efficiency of about 25% or higher, preferably 35% or higher. In one embodiment, OPO 800 is capable of receiving pump laser input pulses 810 at a wavelength of from 525-535 nm and having a pulse energy of 100 mJ/pulse to 5J/pulse, and outputting OPO signal pulses 850 having a wavelength of from 620 nm to 720 nm and a pulse energy of about 50 mJ/pulse to about 2.5 J/pulse. In one embodiment, OPO 800 is capable of receiving pump laser input pulses 810 at a wavelength of from 525-535 nm and having a pulse energy of 100 mJ/pulse to 1 J/pulse, and outputting OPO signal pulses 850 having a pulse energy of about 25 mJ/pulse to about 500 mJ/pulse. In some embodiments, the OPO is capable of outputting both OPO signal pulses 850 and OPO idler pulses 860. In some embodiments, all or a portion of the OPO idler pulses are absorbed in the nonlinear crystal 830. In one embodiment, the nonlinear crystal may absorb from 10-75% of the OPO idler pulse energy, more preferably from 20-60% of the OPO idler pulse energy.

The signal and idler wavelengths $\lambda_s$ and $\lambda_i$ are related to the pump wavelength $\lambda_p$ by energy conservation through the equation $$\frac{1}{\lambda_p} = \frac{1}{\lambda_s} + \frac{1}{\lambda_i}$$

For a given pump wavelength, increasing the signal wavelength will decrease the idler wavelength and vice versa. In cases where optimization of the signal is desired, idler absorption may be used to reduce the $M^2$ of the signal (i.e., to improve signal quality) and the OPO may be adjusted to a signal wavelength where the idler experiences sufficient absorption to reduce the $M^2$ to support practical beam delivery to the patient surface. When the OPO is located within the housing of the system, an $M^2$ of ~100 is desirable to allow for a reasonably narrow arm diameter that such that the arm is ergonomic and not too costly. Even when the OPO is located in the applicator, it may be desirable to use idler absorption to help limit the $M^2$ in order to support a practical working distance and avoid the need for high numerical aperture optics within the applicator.

In one embodiment, BBO is used for the OPO crystal material since the transmission of BBO drops gradually from 100% at 2000 nm to <5% at 3500 nm. Using the equation above, we see that signal wavelengths from 630 to 730 nm will produce idler wavelengths of between 3420 and 1961 nm for a 532 nm pump. Higher idler absorption improves the $M^2$ but will also reduce the signal output energy. Therefore, a range of red wavelengths are possible and can be selected depending on the relative importance of signal pulse energy and $M^2$ for a given application. In on embodiment, transmission through an articulated arm facilitated by selection of 670 nm as the OPO signal wavelength, in which case the $M^2$ will be ~100 and single-pass idler absorption is ~30%.

In one aspect, the present disclosure provides an OPO for use in a dermatological laser treatment system for treating at least one of sebum tissue (e.g. the sebaceous glands) and collagen tissue of a patient. The system includes at least one OPO capable of producing OPO output pulses having a wavelength selected to damage sebum tissue for treating active acne or collagen (e.g., for treating wrinkles). In some embodiments, separate OPOs are provided for targeting sebum tissue and collagen, e.g., a first OPO having an emission wavelength targeting sebum, and a second OPO with an emission wavelength targeting collagen.

Figure 9:
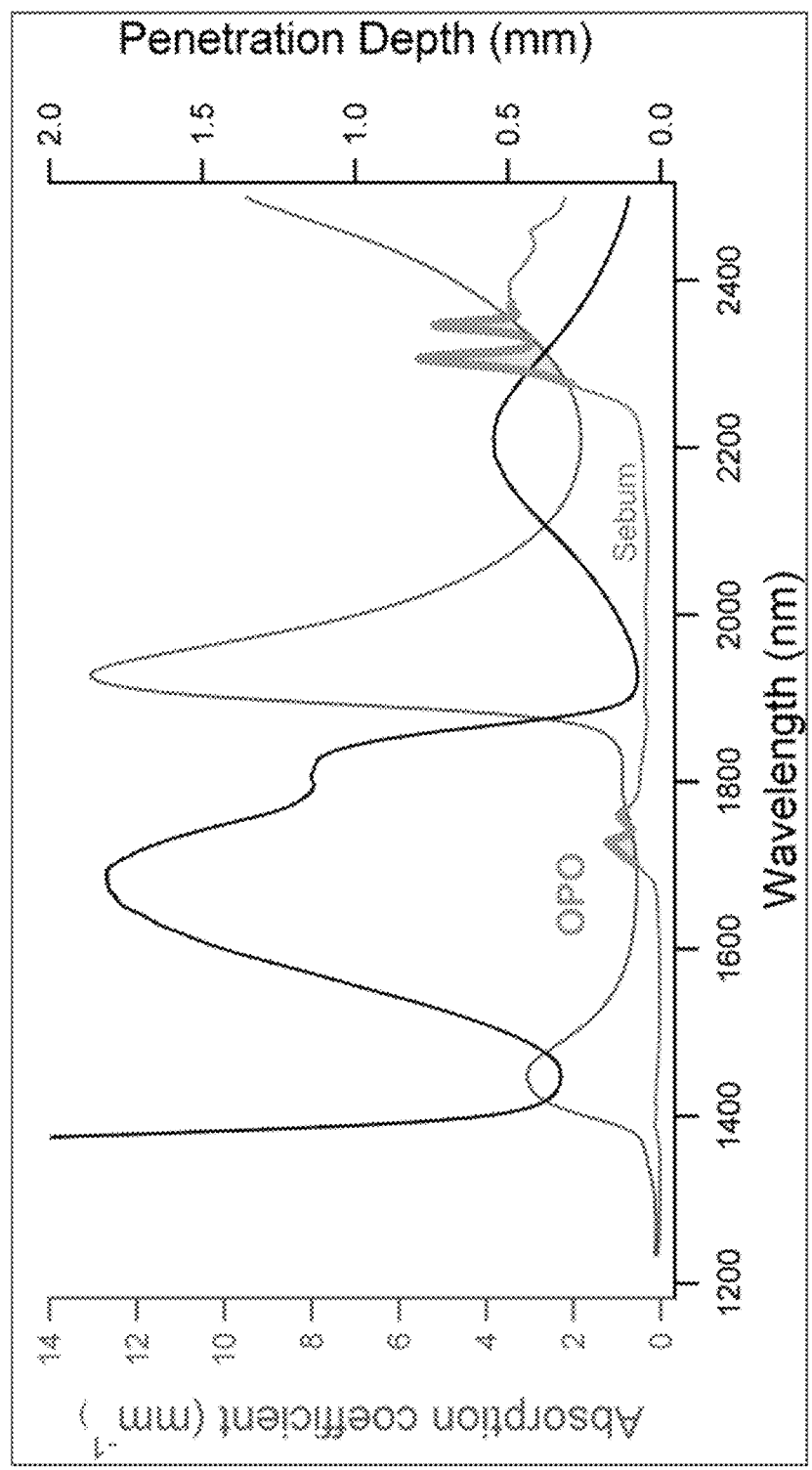
FIG. 9 is a graph illustrating the absorption coefficients of sebum and water for various wavelengths of light.

FIG. 9 is a graph illustrating the absorption coefficients for sebum and water at various wavelengths. For clarity, the curve showing a peak at approximately 1900 nm is the absorption coefficient for water, while the curve showing a double peak between 2200 and 2400 nm is the absorption coefficient for sebum. Both of the absorption coefficient curves are read on the left-side vertical scale. The curve showing a large peak between 1600 and 1700 nm is the penetration depth of light in water, which is read on the right-side vertical scale. As shown in FIG. 9, there are wavelength ranges, with peaks near 1726 nm and about 2305 nm, in the absorption spectrum of sebum at which the absorption coefficient exceeds that of water. More specifically, the absorption coefficient of sebum tissue exceeds that of water at wavelengths of about 1700-1770 nm, and at wavelengths of about 2280-2360 nm. Wavelengths within these wavelength ranges offer the possibility to selectively damage the sebum-filled glands without harming surrounding non-sebum tissues, for which the predominant chromophore is water. It is believed that laser pulses of about 10 J and having a pulse duration less than 200 msec are capable of targeting sebum at a wavelength of about 1726 nm.

Figure 10:
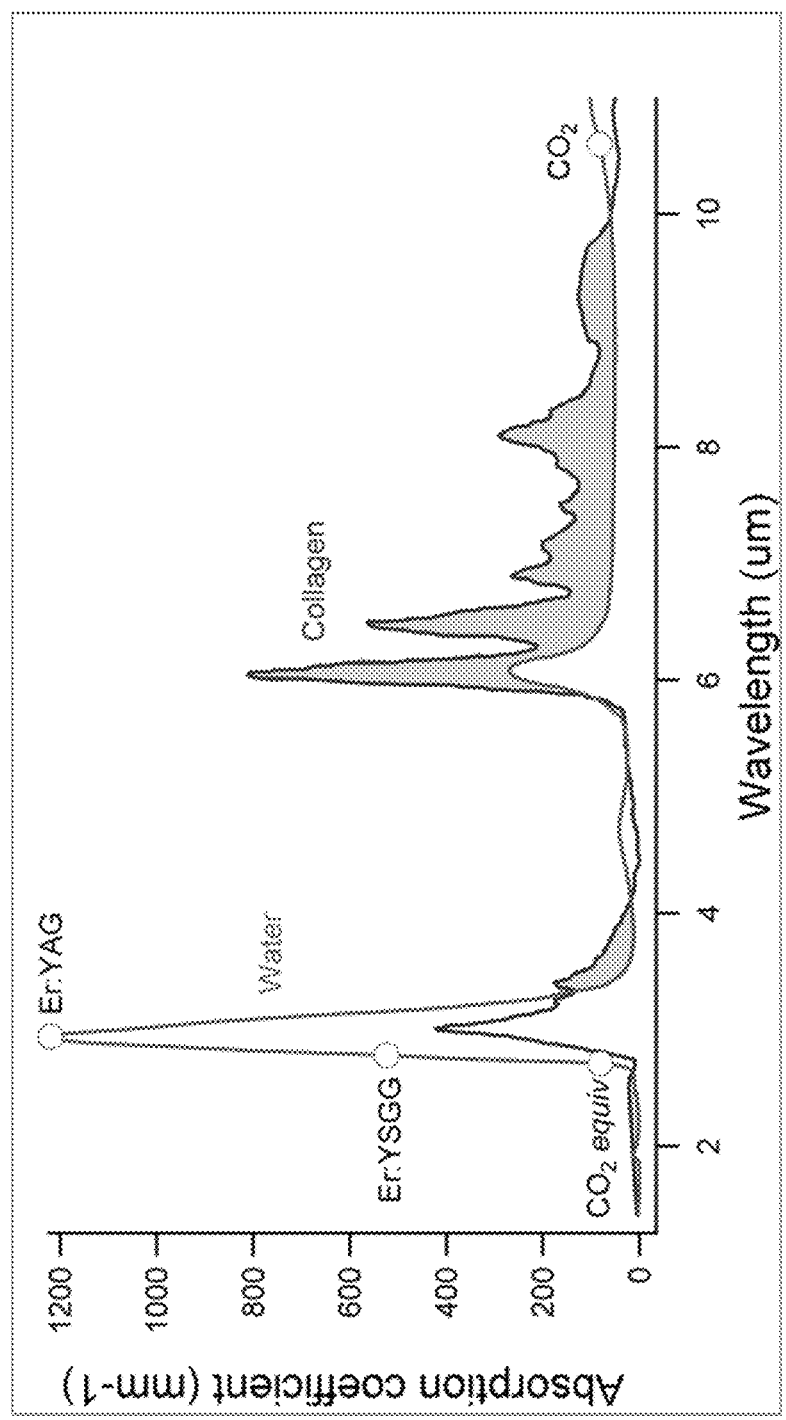
FIG. 10 is a graph illustrating the absorption coefficients of collagen and water at various wavelengths of light.

FIG. 10 is a graph illustrating the absorption coefficients for collagen and water at various wavelengths. FIG. 10 demonstrates that there are wavelength ranges, with peaks near 6049 nm and about 6476 nm, in the absorption spectrum of collagen at which the absorption coefficient exceeds that of water. More specifically, the absorption coefficient of collagen tissue exceeds that of water at wavelengths of about 5900-9500 nm. Wavelengths within these wavelength ranges offer the possibility to selectively damage the collagen without harming surrounding non-collagen tissues, for which the predominant chromophore is water. It is believed that skin resurfacing using embodiments of the present invention to target collagen may involve pulse durations of 0.5-10 msec to selectively target collagen at the foregoing wavelengths.

Figure 12:
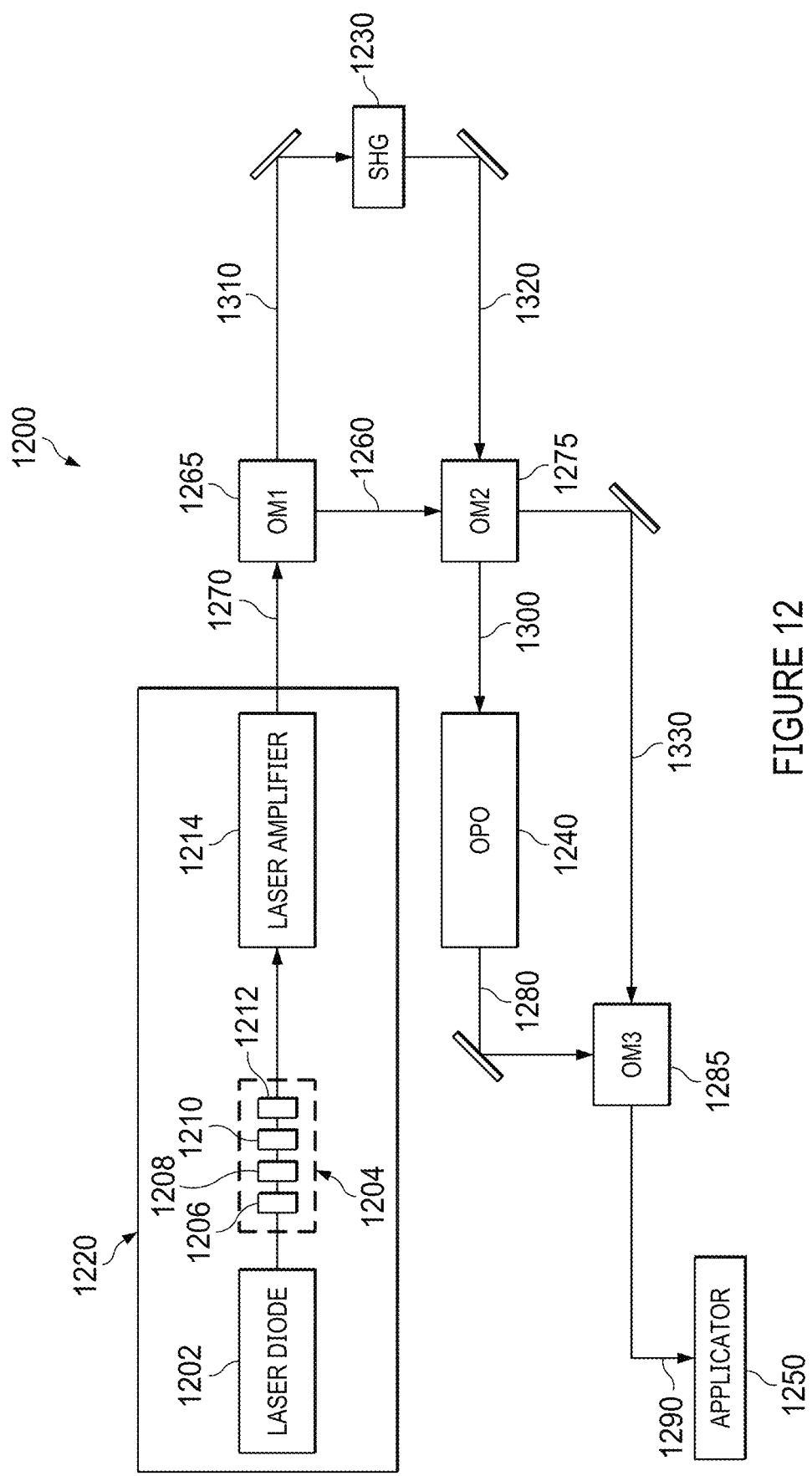
FIG. 12 is a block diagram of an embodiment of a system for treatment of dermatological tissue using pulsed laser light according to one embodiment of the present disclosure.

FIG. 12 discloses simplified block diagram illustration of a dermatological laser treatment system 1200 that may be used to provide treatments for medical conditions involving targeting of sebum and/or collagen. In one embodiment, producing picosecond pulses and having one or more OPOs tuned to a wavelength in the ranges noted in connection with FIGS. 9 and 10 may be used to treat sebum or collagen. The system 1200 includes a laser engine 1220 to generate and output high-energy pulsed laser light a one of a plurality of desired wavelengths on an output path 1270. Although different laser engines are disclosed and described herein, such descriptions should not be construed as limiting or excluding others. Persons of skill in the art, having the benefit of the present disclosure, will appreciate that a variety of different materials, designs and techniques may be used to generate high-energy laser pulses, and unless specifically excluded by the scope of the claims, all are considered to be within the scope of this disclosure.

In one embodiment, laser engine 1220 may comprise a diode laser 1202, a microlaser 1204, and a laser amplifier 1214 to produce pulses having a first wavelength of from 500-1200 nm, a pulse width (PW) of 10 psec to 10 nsec, and a first pulse energy (PE) of 100 mJ/pulse to 5 J/pulse. It will be appreciated that a variety of pulse widths and pulse energies may be used to produced high-energy laser pulses at the foregoing wavelengths and having a peak power in the range of 250 MW or higher.

In one embodiment, the laser engine 1220 may operate in a first treatment mode that is a pulse mode of operation, and may produce individual treatment pulses at a pulse frequency of 0.1 Hz to 100 Hz. In one embodiment, the laser engine 1220 may operate in a second treatment mode that is a burst mode of operation to produce bursts of laser pulses at a burst frequency of 1-100 Hz. Each burst comprises a plurality of individual pulses having a pulse frequency greater than 100 Hz, and in some embodiments greater than 1000 Hz. The bursts have a burst duration of 500 μsec to 50 msec, and a burst energy of from 10 mJ to 20 J.

A laser engine controller (not shown) may be provided in some embodiments to allow a user to select one of the pulse mode of operation or the burst mode of operation. The laser engine controller may include one or more of hardware (e.g., a microprocessor), software, or firmware to control the function and operation of one or more components of the laser engine. In some embodiments a user interface (not shown) may be coupled to the laser engine controller, and the user may select one of the first or second treatment mode, and may control one or more of the foregoing parameters of the laser engine pulses or pulse bursts, via the user interface.

Referring again to FIG. 12, the dermatological laser treatment system 1200 includes an OPO 1240 that is adapted to receive pulsed laser light from the laser engine 1220 along output paths 1270, 1260, 1300. As noted above, OPOs produce simultaneous emission of pulses at an OPO signal wavelength and an OPO idler wavelength when pumped by laser light from the laser engine 1220. The OPO may be constructed and arranged to generate OPO output pulses having a second wavelength selected from a) a wavelength at which sebum tissue has a higher absorption coefficient than water and b) a wavelength at which collagen tissue has a higher absorption coefficient than water. Depending upon its construction and tuning, the OPO 1240 may use either of the OPO signal pulses and the OPO idler pulses as OPO output pulses. The OPO 1240 outputs the output pulses (whether signal or idler wavelength pulses) along an output path 1280.

The dermatological laser treatment system 1200 also includes an applicator 1250 adapted to receive and apply (e.g., using one or more optical multiplexers 1265, 1275, 1285), one of the pulsed laser light output from the laser engine 1220 and the OPO 1240 for application to a target tissue of a patient. As shown in FIG. 12, applicator 1250 may receive pulsed laser light from the laser engine 1220 along optical path 1270, 1260, 1275, 1330, 1290, and may receive pulsed light from OPO 1240 along optical path 1280, 1290. In one embodiment, the applicator may apply the pulsed laser light from the laser engine 120 to a third target body tissue that is neither sebum tissue nor collage tissue. Based on the wavelength output from the OPO 1240, the applicator may receive the OPO output pulses and apply them to a target body tissue comprising sebum tissue or collagen tissue.

In some embodiments (not shown) multiple OPOs 1240 may be provided to enable the dermatological laser treatment system 1200 to generate a variety of treatment wavelengths for targeting a variety of tissue types. Although OPOs may in some embodiments be tunable by adjusting their position or temperature, a given OPO may be tunable only in a particular wavelength range. For example, an OPO 1240 designed to target sebum tissue may not be adjustable to generate wavelengths having sufficient power to target collagen tissue, and vice versa. Accordingly, in one embodiment (not shown) a first OPO 1240 is provided to receive pulsed laser light from the laser engine 1220 at a first wavelength and to generate OPO output pulses having a second wavelength at which sebum tissue has a higher absorption coefficient than water, and a second OPO (not shown) is also provided to receive pulsed laser light from the laser engine 1220 at the first wavelength and to generate OPO output pulses having a third wavelength at which collagen tissue has a higher absorption coefficient than water. Additional optical multiplexers (not shown), similar to optical multiplexers 1265, 1275, 1285, may be provided to enable a user to select an optical path to input light from one of the laser engine 1220 and the SHG 1230 into one of the first OPO 1240 and the second OPO. For example, laser light from the SHG 1230 may be input to the first OPO 124 along optical path 1270, 1310, 1320, 1300. A similar optical path (not shown) may be provided using optical multiplexers to allow light from the laser engine 1220 or the SHG 1230 to be input to the second OPO (not shown). In a still further embodiment (not shown), additional optical multiplexers may be provided to enable an output from one of the first OPO 1240 and the second OPO to be used as an input into the other of the first OPO 1240 and the second OPO to provide additional user-selectable output wavelengths from the system 1200.

In a still further embodiment, a third OPO (not shown) is provided to target tissue that is neither sebum nor collagen. The third OPO may receive pulsed laser light from the laser engine 1220 at the first wavelength and to generate OPO output pulses having a fourth wavelength that is a wavelength at which water has a higher absorption coefficient than sebum tissue and collagen tissue. In another embodiment (not shown) the third OPO may receive laser light from the SHG 1230. In specific embodiments, the second wavelength is a wavelength within one of a first range of from 1700-1770 nm and a second range of from 2280-2360 nm, the third wavelength is a wavelength within a third range of 5900-9500 nm; and the fourth wavelength is a wavelength within one of a fourth range of from 1400-1850 nm, a fifth range of from 1910-1950 nm, and a sixth range of from 2600-3500 nm In multi-OPO embodiments, the dermatological laser treatment system 1200 may comprise an OPO selector (not shown), allowing a system user to select one of the first OPO 1240, the second OPO (not shown), the third OPO (not shown), etc., to receive pulsed laser light from the laser engine 1200 and to generate OPO output pulses for application to a specific target tissue type. The selector may be provided as part of a user interface, previously noted. In other embodiments, the OPO selector may enable a user to select one of the first OPO 1240, second OPO, third OPO, etc., to receive pulsed laser light from one of the laser engine 1200, the SHG, and another of the first OPO 1240, the second OPO, the third OPO, etc., to generate additional desired wavelength(s) to treat different types of target tissue.

Referring again to FIG. 12, in some embodiments the dermatological laser treatment system 1200 may comprise a second harmonic generator (SHG) 1230. The SHG 1230 may be similar to SHG 630 discussed in connection with FIG. 6, and receives the laser pulses from the laser engine 1220 and generates second harmonic laser pulses with a wavelength that is half that of the pulses received from the laser engine 1220. Many different crystals, such as potassium titanyl phosphate (KTP), lithium tetraborate (LBO), and potassium dihydrogen phosphate (KDP) may be used to generate the second harmonic of the first wavelength of the pulses from the laser engine 1220, depending upon the first frequency and other system needs.

In embodiments incorporating a SHG 1230, the dermatological laser treatment system 1200 may be capable of delivering, via applicator 1250, multiple wavelengths of treatment light to the target tissue. In the single-OPO system 1200 of FIG. 12, the user may select (e.g., using one or more optical multiplexers 1265, 1275, 1285), optical pulses for application to the skin of a patient using the applicator 1250. The pulses may be selected to have one of a first wavelength output from the laser engine 1220 (along output path 1270, 1260, 1330, 1290); one or more second wavelengths (e.g., an OPO signal wavelength or OPO idler wavelength) from the OPO 1240 (along output path 1280, 1290); a third wavelength output from the SHG 1230 as the second harmonic of the first wavelength (along path 1320, 1330, 1290), and a one or more for fourth wavelengths that are output from the OPO 1240 when pumped by the SHG 1230 output pulses instead of the laser engine 1220 output pulses (along path 1320, 1300, 1280, 1290. Where multiple OPOs are used (not shown) it will be appreciated that a still greater number of selectable wavelength options will be available to a user to treat a target tissue.

Referring again to FIG. 12, additional details of some laser engine 1220 embodiments are provided. Laser diode 1202 is adapted to output pulsed laser light having a selected laser diode wavelength, which may be selected for optimally pumping microlaser 1204. In one embodiment, the laser diode wavelength is in the range of 808-880 nm, and the laser diode has sufficient peak power that the pulse repetition rate of the microlaser 1204 is greater than 100 Hz and more preferably greater than 1000 Hz. Microlaser 1204 is adapted to receive the pulsed laser light output from the laser diode 1202 and to output pulsed laser light having the first wavelength of from 500-1200 nm, a pulse width (PW) of 10 psec to 10 nsec, and a first pulse energy (PE) of 100 mJ/pulse to 5 J/pulse. In one embodiment, the microlaser includes an input coupler 1206 comprising a mirror having a high transmission at the selected laser diode wavelength and a high reflectance at the first wavelength, a nonlinear crystal 1208 (e.g., Nd:YAG) having a length of 2-10 mm, and a saturable absorber 1210 (i.e., a $Cr^{4+}$:YAG crystal acting as a Q-switch) with an unsaturated transmission between 5 and 40%. In preferred embodiments, the saturable absorber 1210 is monolithically bonded to the nonlinear crystal 1208. The microlaser 1204 also includes an output coupler 1212 having a transmission of the first wavelength of from about 25-75%, and at least 10% greater transmission on the orthogonal, non-lasing polarization. In one embodiment, the output coupler 1212 may comprise a grating waveguide mirror. Laser engine 1220 also includes a laser amplifier 1214 to amplify the output pulses from the microlaser 1204. In one embodiment laser amplifier 1214 is a multi-stage amplifier comprising laser diode or flashlamp pumped Nd:YAG laser rods such that the total stored energy for 200 msec of pumping exceeds 10 J, and preferably greater than 20 J. In such an embodiment, the output of the laser amplifier 1214 comprises 200 msec bursts of 1064 nm, picosecond duration pulses with a frequency (or repetition rate) defined by the microlaser. Notwithstanding the foregoing specific examples of amplifier designs, it will be appreciated that other amplifier designs may be used and are considered within the scope of the present disclosure.

Figure 11:
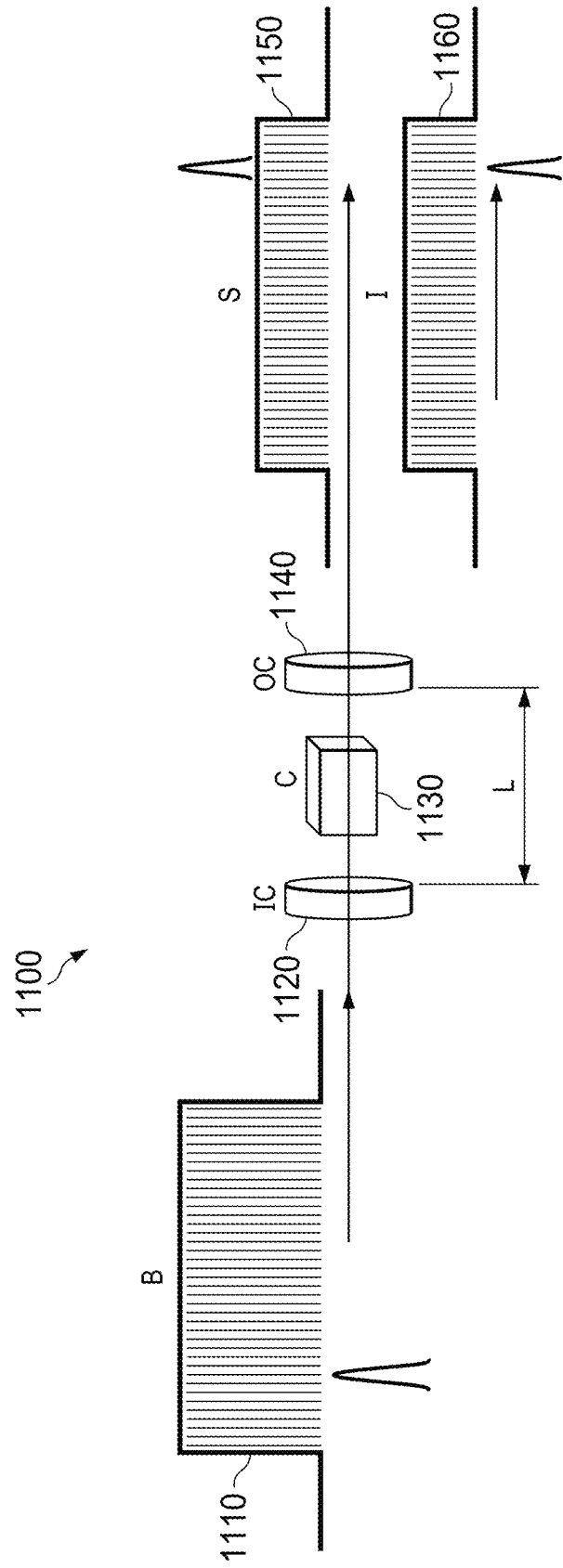
FIG. 11 is a block diagram of one embodiment of an OPO of the present disclosure.

As noted, in some embodiments the dermatological laser treatment system 1200 may provide therapy pulses in one or both of a pulse mode and a burst mode. The figures herein illustrate OPO designs that may be used in certain embodiments of OPO 1240, whether operating in pulse mode or burst mode (FIG. 11). In the following discussion, numbers 800-860 refer to structures in an OPO design according to FIG. 8, while numbers 1100-1160 refer to structures in an OPO design according to a burst mode of operation in FIG. 11. In particular, an OPO 800, 1100 may be used as an OPO 1240 in dermatological laser treatment systems 1200 (FIG. 12). The OPO 800, 1100 includes an input coupler 820, 1120 for receiving input pulses from a laser engine (e.g., laser engine 1220) having a first wavelength. In one embodiment, the input pulses have a pulse width of 10 psec-100 nsec and a first wavelength. The input coupler 820, 1120 comprises a mirror having a high transmission at the first wavelength and a high reflectance at one of the OPO signal wavelength and the OPO idler wavelength.

OPO 800, 1100 also includes a resonant cavity including a nonlinear crystal 830, 1130 that induces parametric amplification of the input pulses to produce OPO signal pulses 850, 1150 and OPO idler pulses 860, 1160 having a second wavelength. It will be appreciated that in FIG. 11 the signal and idler pulses 1150, 1160 are pulses within a pulse burst, produced from a corresponding input burst (B) 1110 comprising a plurality of pulses separated by a short time interval. In different embodiments, one of the signal or idler pulses is output from the OPO 800, 1110 as OPO output pulses which may be provided to treat a target tissue type. In one embodiment, the OPO is designed and constructed such that the second wavelength is selected from a) a wavelength at which sebum tissue has a higher absorption coefficient than water and b) a wavelength at which collagen tissue has a higher absorption coefficient than water. In one embodiment, the wavelength is within one of a first range of from 1700-1770 nm, a second range of from 2280-2360 nm, and a third range of 5900-9500 nm. In one embodiment, the nonlinear crystal 830, 1130 has a crystal length of 5-40 mm and comprises one of beta barium borate (BBO), lithium niobate (LiNbO3), potassium titanyle arsenate (KTA), potassium titanium oxide phosphate (KTP) and zinc germanium phosphide (ZGP).

Finally, OPO 800, 1100 includes an output coupler 840, 1140 comprising a mirror having a high reflectance at the first wavelength and transmitting a selected portion of the second wavelength. The output coupler 840, 1140 may be constructed to achieve a desired transmission of the second wavelength from, e.g., 10-99%, preferably 25-75%, more preferably 40-60%.

OPOs 800, 1100 may be part of an OPO system that may include an adjustment element operable by a user to adjust the second (output) wavelength of the OPO output pulses (e.g., the OPO signal or idler wavelength, depending upon the OPO design). The adjustment element may comprise one or both of a) a crystal angle positioner coupled to the nonlinear crystal, wherein the crystal angle positioner is capable of varying the angle of incidence of the nonlinear crystal to the beam axis of the OPO input pulses to adjust the second wavelength and b) a temperature selector to adjust the temperature of the nonlinear crystal to a desired temperature.

In one embodiment, the OPO output pulses may comprise the OPO signal pulses, and the OPO signal pulse wavelength may be selected to correspond to an OPO idler wavelength for which a portion of the energy of the idler pulses is at least partially absorbed by the nonlinear crystal.

In a specific example, continuing the 1064 nm laser engine output example described in connection with the laser amplifier 1214, the 1064 bursts may be used to directly pump an OPO 1240, or may be used to pump an LBO (lithium triborate) or KTP SHG crystal to produce 532 nm emission which is then used to pump the OPO. In one embodiment, OPO 1240 output pulses or bursts of 1726 nm laser light may be generated by coupling output bursts of 532 nm, 750 psec pulses, using input coupler 1120, into a BBO (barium borate) nonlinear crystal 1130 laser cavity having a length of 5-20 mm that is oriented or positioned to produce OPO signal and idler wavelengths of 769 nm and 1726 nm, respectively. Input coupler 1120 is designed for high transmission at 532 nm, and high reflection at 769 and 1726 nm. Output coupler 1140 is designed to by high reflectance at 769 nm and partially reflective (e.g., 50-75%) at 1726 nm.

In a second example, a 1064 nm, 200 msec burst of 750 psec pulses from laser engine 1220 is coupled through input coupler 1120 into a BBO or LiNbO3 nonlinear crystal 1130 that is oriented to produce OPO signal and idler wavelengths of 1726 nm and 2774 nm, respectively. The input coupler 1120 is designed for high transmission at 1064 nm and high reflection at 1726 and 2774 nm, while output coupler 1140 is designed to be high reflectance at 2774 nm and partially reflective (e.g., 50-75%) at 1726 nm.

In another embodiment, the foregoing OPO could also be tuned by adjusting the crystal angle by approximately 1 degree to produce signal and idler wavelengths of 1550 and 3394 nm, respectively. In further embodiments, the foregoing OPO could be tuned by adjusting the crystal angle to produce signal and idler wavelengths of 1667 and 2940 nm, respectively, or to produce signal and idler wavelengths of 1927 and 2376 nm, respectively. Wavelengths of 1550 and 2940 nm are frequently used for non-ablative and ablative skin resurfacing. Laser emission at 1927 nm is used for skin resurfacing and also for treating pigmented lesions. These applications require laser exposure times between 0.5 to 100 msec which can again be achieved by burst mode operation of the laser source. As shown by these examples, the OPO laser in systems disclosed herein can be act as a tunable light source to target multiple applications including acne, wrinkles, scars, melisma, dyschromia, tattoos, actinic keratosis, and pigmented lesions.

As another example, multiple OPOs may be used in series to produce wavelengths to target collagen in the 6000 nm region. For example, the 1064 nm microlaser 1204 with laser amplifier 1214 described above can be used to pump an OPO 1240 using two KTP crystals to generate OPO output pulses around 2000 um from a first OPO 1240. This emission can then be used to pump a second OPO (not shown) using a ZGP nonlinear crystal 1130 that may be adjusted (or tuned) to produce emission of from 6000 to 10,000 nm from 6 to 10 um by adjusting the crystal angle of the first or second OPO. Skin resurfacing may be done using a fractionated array of laser spots, where the exposure duration at each spot is in the range of 0.5 to 100 msec to limit thermally damaging adjacent tissue. This can again be achieved by burst mode operation of the laser source.

In various embodiments, the present invention relates to the subject matter of the following numbered paragraphs.

The particular embodiments disclosed above are illustrative only, as the invention may be modified and practiced in different but equivalent manners apparent to those skilled in the art having the benefit of the teachings herein. Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept, spirit and scope of the invention. Examples are all intended to be non-limiting. It is therefore evident that the particular embodiments disclosed above may be altered or modified and all such variations are considered within the scope and spirit of the invention, which are limited only by the scope of the claims.

What is claimed is:

1. A dermatological treatment system for treating a plurality of skin conditions using pulsed laser light having a selected wavelength, comprising:
    a laser engine adapted to output pulsed laser light having a first wavelength in one of the visible and near-infrared regions of the electromagnetic spectrum, a pulse width of at least 10 psec, and a first pulse energy of at least 100 mJ/pulse;
    at least one optical parametric oscillator (OPO) adapted to receive pulsed laser light from the laser engine and to generate OPO output pulses having a second wavelength selected from a wavelength at which sebum tissue has a higher absorption coefficient than water and a wavelength at which collagen tissue has a higher absorption coefficient than water, wherein the OPO output pulses comprise one of OPO signal pulses and OPO idler pulses; and
    an applicator adapted to receive and apply a selected one of the pulsed laser light output from the laser engine and the OPO output pulses to a target body tissue.

2. The dermatological treatment system of claim 1, wherein the laser engine is adapted to operate in one of a first treatment mode and a second treatment mode,
    wherein in the first treatment mode the laser engine outputs laser pulses at a pulse frequency of from 0.1 Hz to 100 Hz; and
    wherein in the second treatment mode the laser engine outputs laser bursts at a burst frequency of 1 Hz to 100 Hz, each laser burst having a burst duration of at least 500 μsec, a burst energy of at least 10 mJ, and comprising a plurality of laser pulses having a pulse frequency of from 0.1 Hz to 100 Hz;
the system further comprising
    a laser engine controller for controlling the operation of the laser engine in the first treatment mode and the second treatment mode.

3. The dermatological treatment system of claim 2, further comprising a user interface coupled to the laser engine controller, wherein the user interface allows a user to select one of the first treatment mode and the second treatment mode, and to control at least one of the pulse frequency and the burst frequency.

4. The dermatological treatment system of claim 1, wherein the at least one OPO comprises:
    a first OPO adapted to receive pulsed laser light from the laser engine and to generate OPO output pulses having a second wavelength at which sebum tissue has a higher absorption coefficient than water, and a second OPO adapted to receive pulsed laser light from the laser engine and to generate OPO output pulses having a third wavelength at which collagen tissue has a higher absorption coefficient than water.

5. The dermatological system of claim 4, further comprising a third OPO adapted to receive pulsed laser light from the laser engine and to generate OPO output pulses having a fourth wavelength that is a wavelength at which water has a higher absorption coefficient than sebum tissue and collagen tissue.

6. The dermatological system of claim 5, further comprising an OPO selector allowing a user to select one of the first OPO, the second OPO, and the third OPO to receive pulsed laser light from the laser engine.

7. The dermatological system of claim 5, wherein the second wavelength is a wavelength within one of a first range of from 1700-1770 nm and a second range of from 2280-2360 nm;

the third wavelength is a wavelength within a third range of 5900-9500 nm the fourth wavelength is a wavelength within one of a fourth range of from 1400-1850 nm, a fifth range of from 1910-1950 nm, and a sixth range of from 2600-3500 nm.

8. The dermatological treatment system of claim 1, the system further comprising:

a second harmonic generator (SHG) adapted to receive the pulsed laser light output from the laser engine and to output pulsed laser light having an SHG output wavelength that is half the first wavelength; and an OPO input selector allowing a user to select one of the pulsed laser light output from the laser engine and the pulsed laser light output from the SHG as the input to the at least one OPO.

9. The dermatological treatment system of claim 8, wherein the OPO input selector comprises at least one optical multiplexer adapted to direct the pulsed laser light output from the laser engine to a selected one of the at least one OPO and the SHG, wherein the user can select an OPO input wavelength by directing laser pulses from one of the laser engine and the SHG as the input to the at least one OPO.

10. The dermatological treatment system of claim 8, further comprising:

a user-selectable first output path located between the laser engine and the SHG, wherein the user may select the first output path to output first laser pulses to the applicator;

a user-selectable second output path located between the SHG and a first OPO of the at least one OPO, wherein the user may select the second output path to output second harmonic laser pulses to the applicator; and a user-selectable third output path located proximate the first OPO signal output, wherein the user may select the third output path to output first OPO signal pulses to the applicator.

11. The dermatological treatment system of claim 1, further comprising an applicator input selector comprising at least one optical multiplexer allowing a user to direct a selected one of pulsed laser light output from the laser engine and OPO output pulses from a selected one of the at least one OPOs to the applicator for application to the target body tissue of the patient.

12. The dermatological treatment system of claim 1, further comprising an adjustment element operable by a user to adjust the second wavelength of the OPO output pulses, wherein the adjustment element comprises at least one of:

a crystal angle positioner coupled to the nonlinear crystal, wherein the crystal angle positioner is capable of varying the angle of incidence of the nonlinear crystal to the beam axis of the OPO input pulses to adjust the second wavelength; and a temperature selector stabilizer to adjust the temperature of the nonlinear crystal to a desired temperature.

13. The dermatological treatment system of claim 1, the system further comprising a housing within which the laser engine is located, wherein one of the at least one OPOs is located in one of the applicator and the housing.

14. A dermatological treatment system for treating a plurality of skin conditions using pulsed laser light having a selected wavelength, comprising:

a laser engine adapted to output first laser pulses having a first wavelength in one of the visible and near-infrared regions of the electromagnetic spectrum, a pulse width of at least 10 psec, and a first pulse energy of up to 10 J/pulse;

a second harmonic generator (SHG) capable of receiving the first laser pulses from the laser engine and generating second harmonic laser pulses having a second wavelength in the visible electromagnetic spectrum;

an optical parametric oscillator (OPO) capable of receiving the second harmonic laser pulses and generating OPO signal pulses having a third wavelength in the visible electromagnetic spectrum and OPO idler pulses having a fourth wavelength in one of the near-infrared and infrared regions of the electromagnetic spectrum;

an applicator capable of receiving a selected one of the first laser pulses, the second harmonic laser pulses, at least one of the OPO signal pulses and the OPO idler pulses, and applying the selected pulses to the skin of a patient;

a user-selectable first output path located between the laser engine and the SHG, wherein the user may select the first output path to output first laser pulses to the applicator;

a user-selectable second output path located between the SHG and the OPO, wherein the user may select the second output path to output second harmonic laser pulses to the applicator; and a user-selectable third output path located proximate the OPO signal output, wherein the user may select the third output path to output one of OPO signal pulses and OPO idler pulses to the applicator.

15. The dermatological treatment system of claim 14, wherein the second harmonic generator is capable of generating second harmonic pulses having a pulse energy in the range of from 50 mJ/pulse to 5 J/pulse.

16. The dermatological treatment system of claim 14, further comprising:

a user-selectable fourth output path located after the OPO, wherein the user may select the third output path to output one of OPO signal pulses and OPO idler pulses to the applicator, and the user may select the fourth output path to output the other of the OPO signal pulses and the OPO idler pulses to the applicator.

17. The dermatological treatment system of claim 14, wherein the OPO is adapted to generate OPO signal pulses having a third wavelength within one of a first range of from 1700-1770 nm, a second range of from 2280-2360 nm, a third range of from 5900-9500 nm.

18. The dermatological treatment system of claim 14, wherein the OPO comprises:
- a resonant cavity including a beta barium borate (BBO) crystal;
- a first mirror coupled to a first end of the resonant cavity;
- a second mirror coupled to a second end of the resonant cavity; and
- an adjustment element operable by the user to adjust the OPO to generate OPO signal pulses having a desired third wavelength and OPO idler pulses having a desired fourth wavelength.

19. The dermatological treatment system of claim 14 comprising:
- a first OPO adapted to receive pulsed laser light from one of the laser engine and the SHG to generate OPO output pulses having a wavelength at which sebum tissue has a higher absorption coefficient than water; and
- a second OPO adapted to receive pulsed laser light from one of the laser engine, the SHG, and the first OPO, wherein the second OPO is adapted to generate OPO output pulses having a wavelength at which collagen tissue has a higher absorption coefficient than water.

20. The dermatological treatment system of claim 1, wherein the applicator comprises a handpiece constructed and arranged to be held in the hand of a user and having an output to apply a selected one of the first laser pulses, the second harmonic laser pulses, and the OPO signal pulses to the skin of a patient, the system further comprising:
- a housing coupled to the handpiece, wherein the laser engine and the SHG are located within the housing, and the OPO is located within one of the housing and the handpiece.

* * * * *